United States Patent
Ogihara et al.

(10) Patent No.: US 9,624,356 B2
(45) Date of Patent: Apr. 18, 2017

(54) ULTRAVIOLET ABSORBER, COMPOSITION FOR FORMING A RESIST UNDER LAYER FILM, AND PATTERNING PROCESS

(71) Applicant: SHIN-ETSU CHEMICAL CO., LTD., Tokyo (JP)

(72) Inventors: Tsutomu Ogihara, Jyoetsu (JP); Daisuke Kori, Jyoetsu (JP)

(73) Assignee: SHIN-ETSU CHEMICAL CO., LTD, Tokyo (JP)

( * ) Notice: Subject to any disclaimer, the term of this patent is extended or adjusted under 35 U.S.C. 154(b) by 0 days.

(21) Appl. No.: 14/794,311

(22) Filed: Jul. 8, 2015

(65) Prior Publication Data

US 2016/0053087 A1 Feb. 25, 2016

(30) Foreign Application Priority Data

Aug. 19, 2014 (JP) ................. 2014-166441

(51) Int. Cl.

| | |
|---|---|
| G03F 7/075 | (2006.01) |
| G03F 7/095 | (2006.01) |
| G03F 7/11 | (2006.01) |
| C08K 3/34 | (2006.01) |
| C07D 251/30 | (2006.01) |
| H01L 21/311 | (2006.01) |
| C08K 5/3492 | (2006.01) |
| G03F 7/09 | (2006.01) |

(52) U.S. Cl.
CPC ........ *C08K 5/34924* (2013.01); *C07D 251/30* (2013.01); *G03F 7/0752* (2013.01); *G03F 7/091* (2013.01); *G03F 7/094* (2013.01); *H01L 21/31138* (2013.01); *H01L 21/31144* (2013.01)

(58) Field of Classification Search
None
See application file for complete search history.

(56) References Cited

U.S. PATENT DOCUMENTS

| 5,632,910 A | 5/1997 | Nagayama et al. | |
|---|---|---|---|
| 6,268,457 B1 * | 7/2001 | Kennedy ................. | C03C 17/30 106/287.13 |
| 6,368,400 B1 * | 4/2002 | Baldwin ................. | C03C 17/30 106/481 |
| 8,481,247 B2 * | 7/2013 | Horiguchi ............... | G03F 7/091 430/271.1 |
| 2007/0004228 A1 * | 1/2007 | Hatanaka ................ | G03F 7/091 438/780 |
| 2007/0238300 A1 | 10/2007 | Ogihara et al. | |
| 2008/0138744 A1 * | 6/2008 | Hatanaka .............. | G03F 7/0392 430/319 |
| 2009/0011366 A1 | 1/2009 | Tsubaki et al. | |
| 2009/0136869 A1 | 5/2009 | Ogihara et al. | |
| 2009/0243018 A1 * | 10/2009 | Karkkainen ........... | C08G 77/04 257/437 |
| 2009/0274974 A1 * | 11/2009 | Abdallah ................ | G03F 7/091 430/270.1 |
| 2010/0040972 A1 | 2/2010 | Tarutani et al. | |
| 2010/0291483 A1 * | 11/2010 | Hamada ................... | G03F 7/11 430/282.1 |
| 2011/0251305 A1 * | 10/2011 | Ueno .................. | C08G 59/306 523/429 |

FOREIGN PATENT DOCUMENTS

| EP | 1560070 | * | 8/2005 |
|---|---|---|---|
| EP | 1939688 | * | 7/2008 |
| EP | 2042927 | * | 4/2009 |
| JP | H07-181688 A | | 7/1995 |
| JP | H07-183194 A | | 7/1995 |
| JP | 2005509913 A | | 4/2005 |
| JP | 2005512309 A | | 4/2005 |
| JP | 2005520354 A | | 7/2005 |
| JP | 2005-300825 | * | 10/2005 |
| JP | 2007520737 A | | 7/2007 |
| JP | 2007302873 A | | 11/2007 |
| JP | 2008281974 A | | 11/2008 |
| JP | 2008281980 A | | 11/2008 |
| JP | 2009053657 A | | 3/2009 |
| JP | 2009126940 A | | 6/2009 |
| JP | 4716037 B2 | | 7/2011 |
| WO | 03044078 A1 | | 5/2003 |
| WO | 2004007192 A1 | | 1/2004 |
| WO | 2005049681 A2 | | 6/2005 |

* cited by examiner

Primary Examiner — Martin Angebranndt
(74) Attorney, Agent, or Firm — Oliff PLC

(57) ABSTRACT

The present invention provides an ultraviolet absorber containing a compound represented by the formula (A-1),

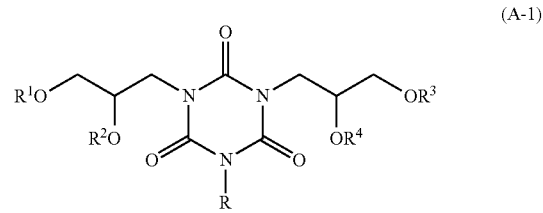

wherein R represents a methyl group, an ethyl group, a propyl group, or an allyl group, and $R^1$, $R^2$, $R^3$, and $R^4$ may be the same or different, and each represent a hydrogen atom, a benzoyl group, a toluoyl group, a naphthoyl group, or an anthranoyl group. By adding the ultraviolet absorber to a composition for forming a resist under layer film, reflection can be suppressed particularly in lithography process by an ultraviolet laser, and a pattern profile can be improved without adverse effects on dry etching mask properties and adhesiveness to a resist pattern.

17 Claims, No Drawings

ULTRAVIOLET ABSORBER, COMPOSITION FOR FORMING A RESIST UNDER LAYER FILM, AND PATTERNING PROCESS

BACKGROUND OF THE INVENTION

Field of the Invention

The present invention relates to an ultraviolet absorber, a composition for forming a resist under layer film containing the same, and a patterning process using the same.

Description of the Related Art

In 1980s, photo-exposure using a g-beam (436 nm) or an i-beam (365 nm) of a mercury lamp as a light source had been widely used in the resist patterning. As a means for finer patterning, shifting to a exposure light having shorter wavelength was assumed to be effective, so that, for the mass production process of DRAM (Dynamic Random Access Memory) with 64 MB (work size of 0.25 µm or less) in 1990s and later ones, a KrF excimer laser (248 nm), whose wavelength is shorter than the i-beam (365 nm), had been used in place of the i-beam as the exposure light source. However, for production of DRAM with integration of 256 MB and 1 GB or higher requiring further finer processing technologies (work size of 0.2 µm or less), a light source having a further shorter wavelength was required, and thus, a photolithography using an ArF excimer laser (193 nm) has been investigated seriously over a decade.

It was expected at first that the ArF lithography would be applied to the fabrication of 180 nm-node devices. However, the KrF excimer lithography survived to the mass production of 130 nm-node devices, so that a full-fledged application of the ArF lithography started from the 90 nm-node. Furthermore, mass production of the 65 nm-node devices is now underway by combining the ArF lithography with a lens having an increased numerical aperture (NA) of 0.9. For the next 45 nm-node devices, further shortening the wavelength of exposure light is progressing, and the $F_2$ lithography with 157 nm wavelength became a candidate.

However, there are many problems in the $F_2$ lithography: cost-up of a scanner due to use of the large quantities of the expensive $CaF_2$ single crystal for a projection lens; extremely poor durability of a soft pellicle, which leads to change of an optical system due to introduction of a hard pellicle; decrease in etching resistance of a resist film, and so forth. Because of these problems, development of the $F_2$ lithography was suspended, and the ArF immersion lithography was introduced.

In the ArF immersion lithography, water having a refractive index of 1.44 is introduced between a projection lens and a wafer by a partial fill method, thereby enabling high speed scanning, and thus, mass production of the 45 nm-node devices is now underway by using a lens with a NA of 1.3.

For the 32 nm-node lithography, lithography with an extreme-ultraviolet beam (EUV) of 13.5 nm-wavelength is considered to be a candidate. Problems to be solved in the EUV lithography are to obtain a higher output power of the laser, a higher sensitivity of the resist film, a higher resolution, a lower line edge roughness (LER), a non-defect MoSi laminate mask, a lower aberration of the reflective mirror, and so forth; and thus, there are innumerable problems to be solved.

Development of the immersion lithography with a high refractive index, another candidate for the 32 nm-node, was suspended because transmittance of LUAG, a candidate for a high refractive index lens, is low, and refractive index of the liquid could not reach an aimed value of 1.8.

As mentioned above, in the photo-exposure used as a general technology, resolution based on the wavelength of the light source is approaching to its inherent limit. Thus, in recent years, patterning through negative tone by organic solvent development that can form a very fine hole pattern, which is not achievable by conventional patterning through positive tone by alkaline development, attracted attention again. This is a process for forming a negative pattern by using a positive resist composition featuring a high resolution by organic solvent development. Furthermore, an attempt to double a resolution by combining two developments, alkaline development and organic solvent development, is under study (Patent Documents 1 to 3).

A multilayer resist method is one of the methods for transferring a lithography pattern to a substrate. In this method, an intermediate film (e.g. a silicon-containing resist under layer film) having etching selectivity different from that of a photoresist film, i.e. a resist upper layer film, is interposed between the resist upper layer film and a substrate to be processed, a pattern is formed with the resist upper layer film, and the pattern is then transferred to the resist under layer film by dry etching using the upper layer resist pattern as a dry etching mask, and further the pattern is transferred to the substrate to be processed by dry etching using the resist under layer film as a dry etching mask.

As a material to be used for such a multilayer resist method, a composition for forming a silicon-containing film has been well known. For example, a silicon-containing inorganic film formed by a CVD method, such as a $SiO_2$ film (Patent Document 4) and a SiON film (Patent Document 5), and a material that can be obtained by spin-coating, such as a SOG (spin-on-glass) film (Patent Document 6) and a cross-linkable silsesquioxane film (Patent Document 7), may be mentioned.

PRIOR ART DOCUMENTS

Patent Documents

Patent Document 1: Japanese Patent Laid-Open Publication No. 2008-281974
Patent Document 2: Japanese Patent Laid-Open Publication No. 2008-281980
Patent Document 3: Japanese Patent Laid-Open Publication No. 2009-053657
Patent Document 4: Japanese Patent Laid-Open Publication No. H07-183194
Patent Document 5: Japanese Patent Laid-Open Publication No. H07-181688
Patent Document 6: Japanese Patent Laid-Open Publication No. 2007-302873
Patent Document 7: Japanese Patent Laid-Open Publication No. 2005-520354

SUMMARY OF THE INVENTION

The present inventors have earnestly investigated on lithography characteristics and stability of a composition for forming a silicon-containing resist under layer film until now, and provided a composition for forming a silicon-containing resist under layer film as disclosed in Japanese Patent No. 4716037 as a dry etching mask material, thereby a silicon-containing resist under layer film excellent in etching selectivity and storage stability could be provided.

However, miniaturization of a semiconductor apparatus not only progresses in horizontal direction for thinning the line width of the substrate pattern, but also progresses toward lamination in vertical direction, i.e. high densification in three-dimension, so that processing in vertical direction becomes important for processing a substrate. Thus, enough film thickness is required for a coating film used as an etching mask, and a dry etching mask becomes necessary also for a rough design pattern, which has been considered not to need a dry etching mask.

Moreover, in the patterning process by photolithography, an antireflective film is occasionally used for the purpose of suppressing reflection of the exposure light, and adding an antireflective agent composed of an organic compound to a composition for forming a resist under layer film, which is a dry etching mask material, has been attempted since before in order to give a function as an antireflective film to the dry etching mask itself (Japanese Patent Laid-Open Publication No. 2005-509913, No. 2005-512309, No. 2007-520737, etc.). However, there is a problem that if the antireflective agent composed of an organic compound is added to the composition for forming a silicon-containing resist under layer film as mentioned above, in general, adhesiveness to a resist pattern is lowered, or etching rate is changed, whereby properties as the dry etching mask becomes inferior.

The present invention has been accomplished in view of the above-described circumstances, and an object thereof is to provide an ultraviolet absorber that can suppress reflection particularly in lithography process by an ultraviolet laser and improve a pattern profile without adverse effects on dry etching mask properties and adhesiveness to a resist pattern, compared with a case using the conventional silicon-containing resist under layer film, when the ultraviolet absorber is added to a composition for forming a resist under layer film.

To solve the above-mentioned problems, the present invention provides an ultraviolet absorber comprising a compound represented by the formula (A-1),

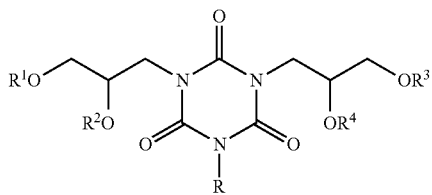

(A-1)

wherein R represents a methyl group, an ethyl group, a propyl group, or an allyl group; $R^1$, $R^2$, $R^3$, and $R^4$ may be the same or different, and each represent a hydrogen atom, a benzoyl group, a toluoyl group, a naphthoyl group, or an anthranoyl group; with the provisos that $R^1$ and $R^2$ are not a hydrogen atom at the same time; $R^3$ and $R^4$ are not a hydrogen atom at the same time; when $R^1$ and $R^2$ are a hydrogen atom and a benzoyl group, $R^3$ and $R^4$ are not a hydrogen atom and a benzoyl group; and when $R^1$ and $R^2$ are a hydrogen atom and a toluoyl group, $R^3$ and $R^4$ are not a hydrogen atom and a toluoyl group.

When such an ultraviolet absorber is added to a composition for forming a resist under layer film, the ultraviolet absorber can suppress reflection by adsorbing ultraviolet rays particularly in lithography process by an ultraviolet laser such as ArF laser and KrF laser, and can improve a pattern profile without adverse effects on dry etching mask properties and adhesiveness to a resist pattern formed on the resist under layer film.

Preferably, three or more of $R^1$, $R^2$, $R^3$, and $R^4$ in the formula (A-1) are each selected from a benzoyl group, a toluoyl group, a naphthoyl group, and an anthranoyl group.

Also, the present invention provides a composition for forming a resist under layer film, comprising the above-described ultraviolet absorber and a polysiloxane.

Such a composition for forming a resist under layer film can form a resist under layer film that can suppress reflection particularly in lithography process by an ultraviolet laser such as ArF laser and KrF laser, and has excellent adhesiveness to a resist pattern formed thereon and excellent dry etching selectivity between the resist pattern formed thereon and an organic under layer film or the like formed thereunder.

The polysiloxane preferably contains one or more members selected from a compound represented by the formula (B-1), a hydrolysate of the compound, a condensate of the compound, and a hydrolysis condensate of the compound,

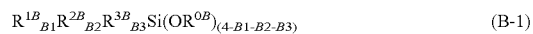

(B-1)

wherein $R^{OB}$ represents a hydrocarbon group having 1 to 6 carbon atoms; $R^{1B}$, $R^{2B}$, and $R^{3B}$ each represent a hydrogen atom or a monovalent organic group; and B1, B2, and B3 are each 0 or 1, and satisfy $0 \leq B1+B2+B3 \leq 3$.

When the composition for forming a resist under layer film contains such a polysiloxane, the above-described adhesiveness and dry etching selectivity are further excellent.

Furthermore, the present invention provides a patterning process comprising the steps of: forming an organic under layer film on a body to be processed by using a coating type organic under layer film material; forming a resist under layer film on the organic under layer film by using the above-described composition for forming a resist under layer film; forming a resist upper layer film on the resist under layer film; forming a resist pattern with the resist upper layer film; transferring the pattern to the resist under layer film by dry etching using the resist pattern as a mask; transferring the pattern to the organic under layer film by dry etching using the resist under layer film to which the pattern has been transferred as a mask; and further transferring the pattern to the body to be processed by dry etching using the organic under layer film to which the pattern has been transferred as a mask.

In this way, the patterning process by the three-layer resist method using the composition for forming a resist under layer film of the present invention enables a fine pattern to be formed on a substrate with high precision.

At this time, the body to be processed is preferably a semiconductor apparatus substrate or a material in which any of a metal film, a metal carbide film, a metal oxide film, a metal nitride film, a metal oxycarbide film, and a metal oxynitride film is formed on the semiconductor apparatus substrate.

Moreover, a metal constituting the body to be processed preferably comprises silicon, titanium, tungsten, hafnium, zirconium, chromium, germanium, copper, silver, gold, aluminum, indium, gallium, arsenic, palladium, iron, tantalum, iridium, molybdenum, or an alloy thereof.

In this way, the patterning process of the present invention can form a pattern by processing the above-described body to be processed.

As mentioned above, when the ultraviolet absorber of the present invention is employed, for example, by adding it to a composition for forming a resist under layer film containing a polysiloxane, a resist under layer film that can suppress reflection by absorbing ultraviolet rays particularly in lithography process by an ultraviolet laser such as ArF laser and KrF laser, and exhibits excellent adhesiveness to a resist pattern formed thereon and high dry etching selectivity to both of the resist pattern formed thereon and an organic under layer film or the like formed thereunder, can be formed. Accordingly, when the formed resist pattern is sequentially transferred to the resist under layer film and the organic under layer film by dry etching process, the pattern can be transferred with a good pattern profile. In this way, the pattern formed in the upper layer resist can be finally transferred to the substrate with high precision.

DETAILED DESCRIPTION OF THE PREFERRED EMBODIMENTS

As mentioned above, it has been desired to develop an ultraviolet absorber that can suppress reflection in lithography process by an ultraviolet laser such as ArF laser and KrF laser and improve a pattern profile without adverse effects on dry etching mask properties and adhesiveness to a resist pattern, compared with a case using the conventional silicon-containing resist under layer film, by adding the same to a composition for forming a resist under layer film.

The present inventors earnestly investigated on the above problems and consequently found that the problems can be solved by adding the ultraviolet absorber of the present invention to a composition for forming a resist under layer film, thereby bringing the present invention to completion.

That is, the present invention is directed to an ultraviolet absorber comprising a compound represented by the formula (A-1),

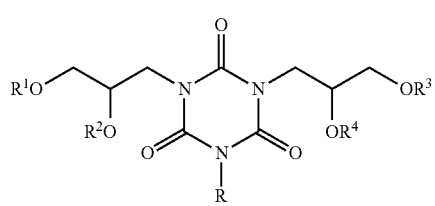
(A-1)

wherein R represents a methyl group, an ethyl group, a propyl group, or an allyl group; $R^1$, $R^2$, $R^3$, and $R^4$ may be the same or different, and each represent a hydrogen atom, a benzoyl group, a toluoyl group, a naphthoyl group, or an anthranoyl group; with the provisos that $R^1$ and $R^2$ are not a hydrogen atom at the same time; $R^3$ and $R^4$ are not a hydrogen atom at the same time; when $R^1$ and $R^2$ are a hydrogen atom and a benzoyl group, $R^3$ and $R^4$ are not a hydrogen atom and a benzoyl group; and when $R^1$ and $R^2$ are a hydrogen atom and a toluoyl group, $R^3$ and $R^4$ are not a hydrogen atom and a toluoyl group.

Hereinafter, the present invention will be described in detail, but the present invention is not limited thereto.

Herein, "Me" represents a methyl group, and "Et" represents an ethyl group.

<Ultraviolet Absorber>

The ultraviolet absorber of the present invention contains the compound represented by the formula (A-1). A benzoyl group, a toluoyl group, a naphthoyl group, and an anthranoyl group of $R^1$ to $R^4$ in the formula (A-1) are groups for absorbing ultraviolet rays (hereinafter, also referred as "ultraviolet-absorbing group"), and by reason of absorption wavelength, a material having a benzoyl group or a toluoyl group is preferred for ArF (193 nm) exposure, and a material having a naphthoyl group or an anthranoyl group is preferred for KrF (248 nm) exposure.

Also, three or more of $R^1$, $R^2$, $R^3$, and $R^4$ in the formula (A-1) are each preferably selected from a benzoyl group, a toluoyl group, a naphthoyl group, and an anthranoyl group.

The compound represented by the formula (A-1) may be specifically exemplified by the following compounds.

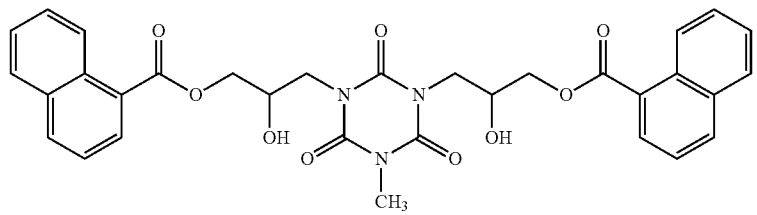

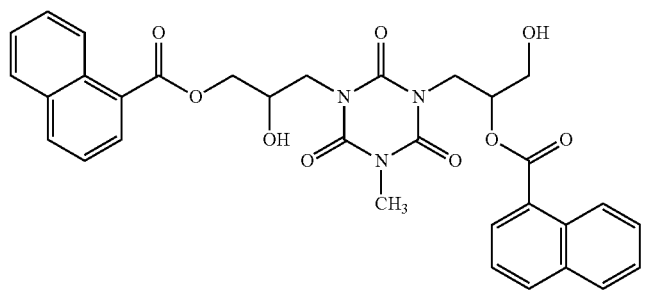

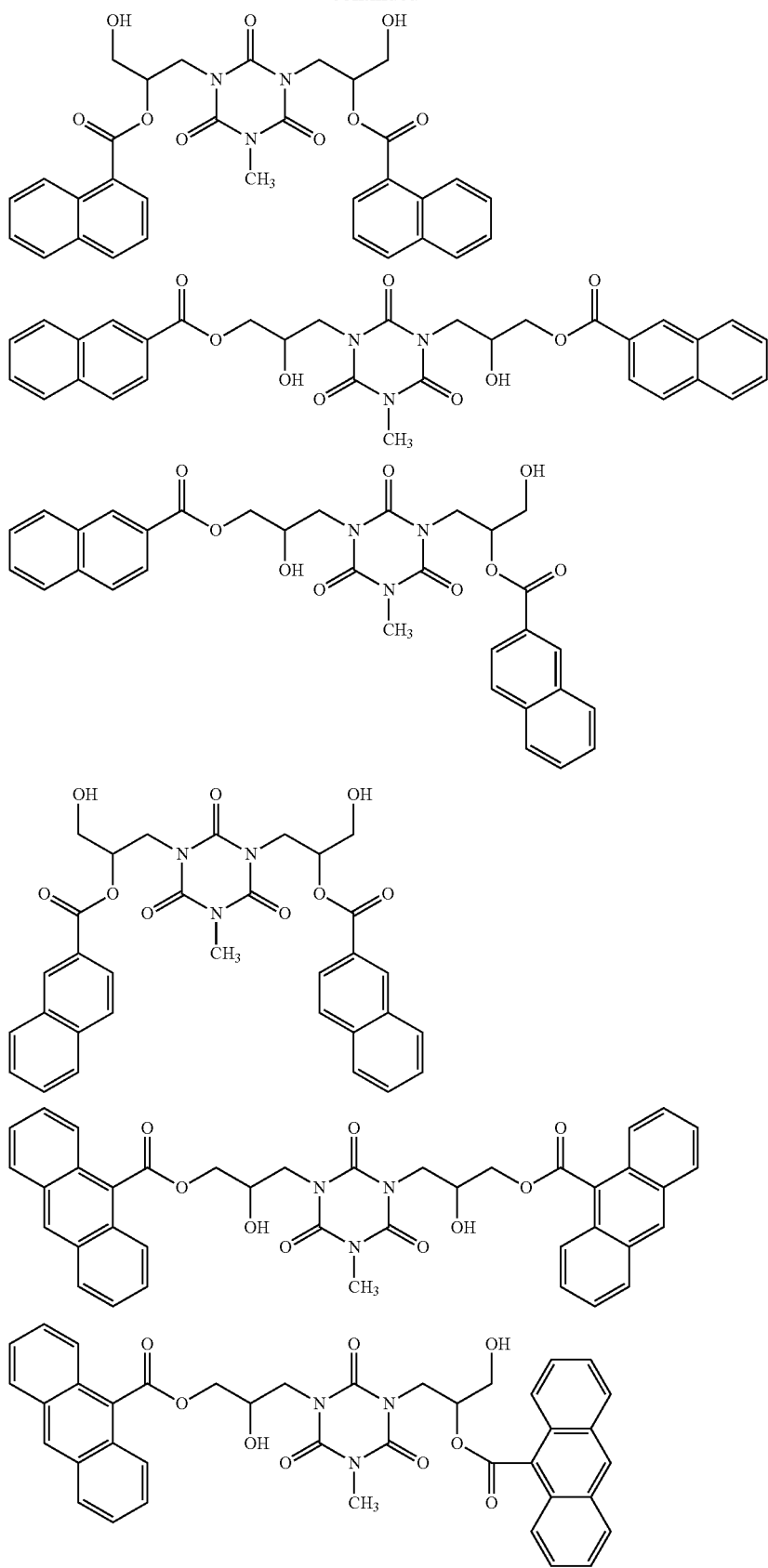

-continued
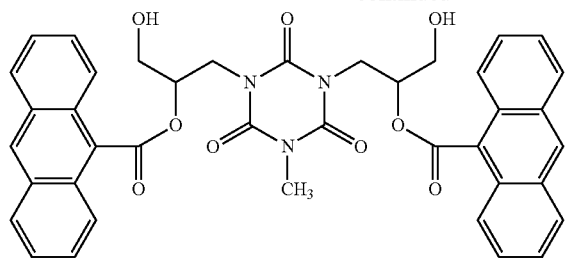
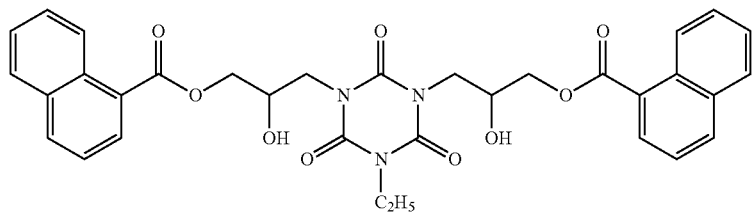
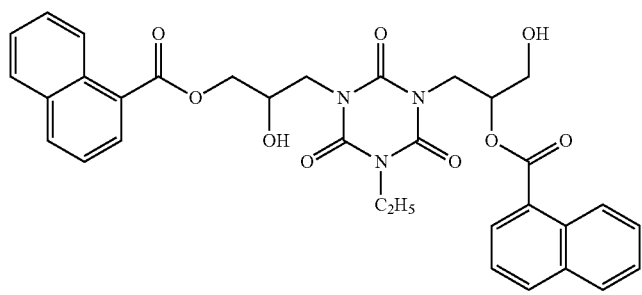
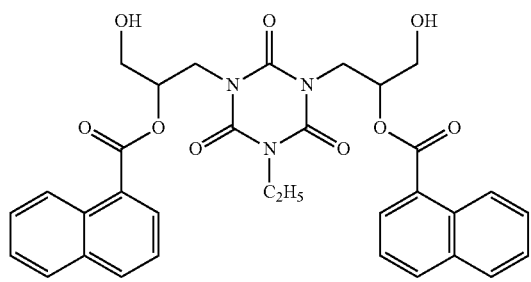
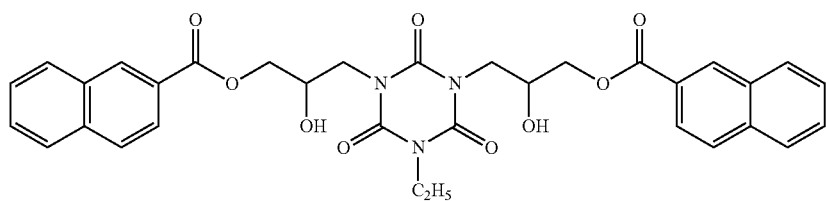
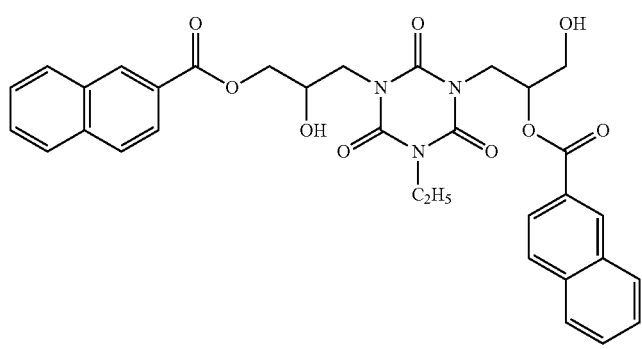

-continued
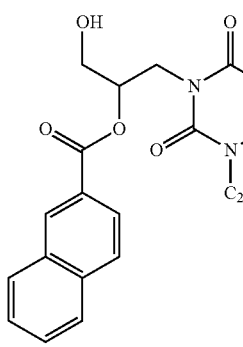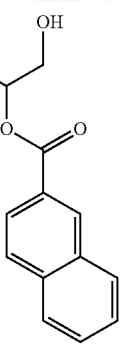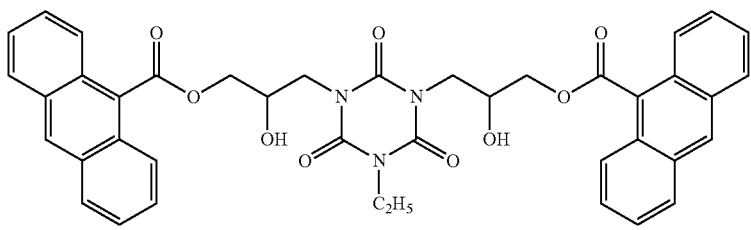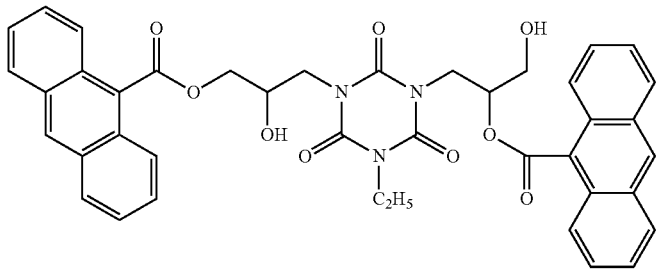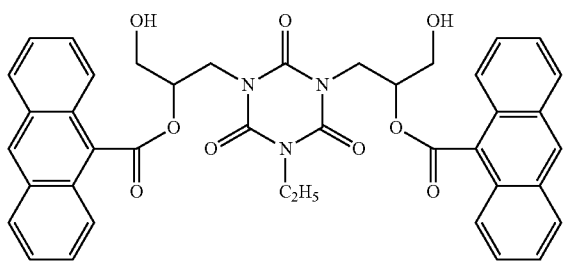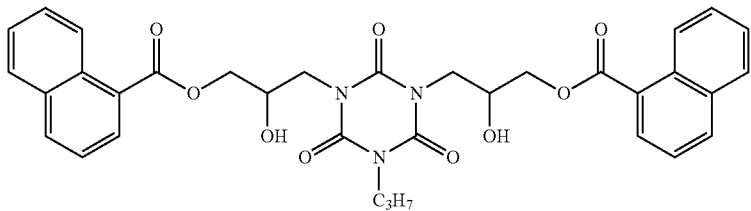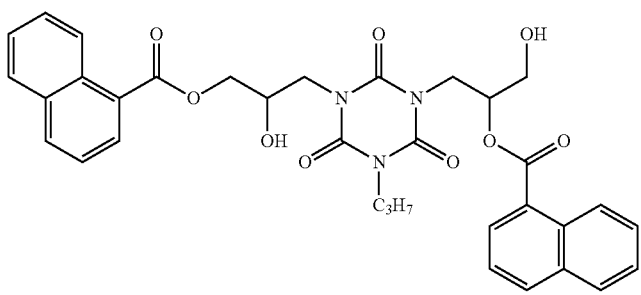

-continued
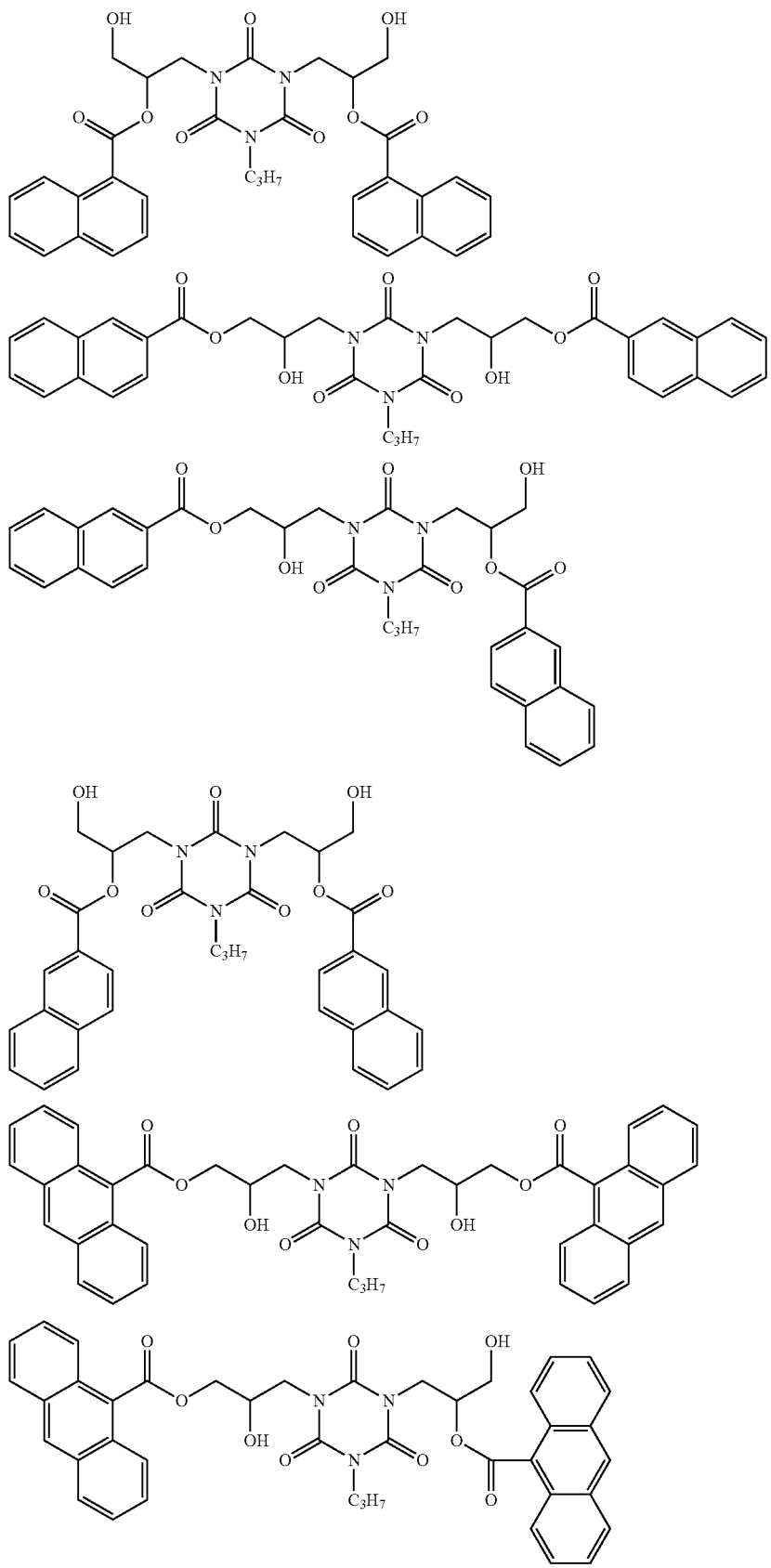

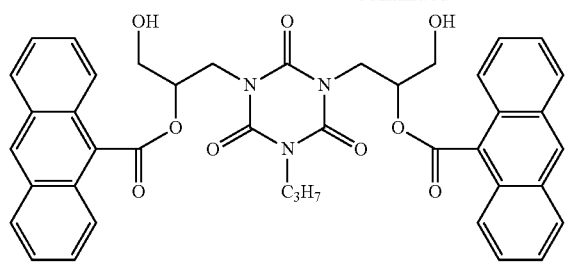
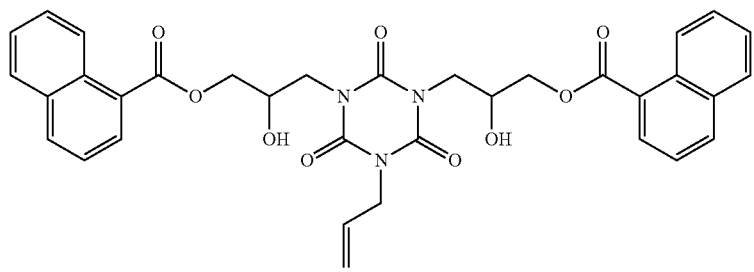
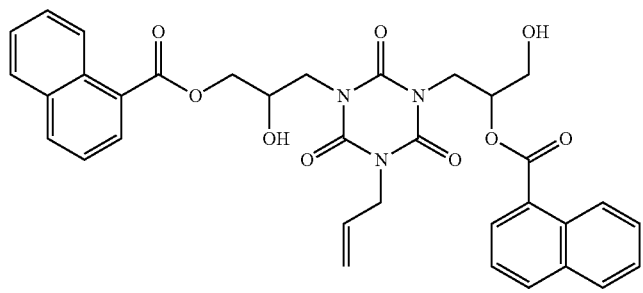
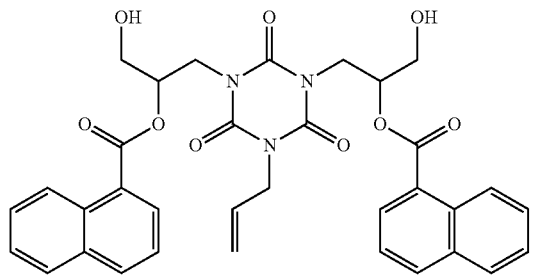
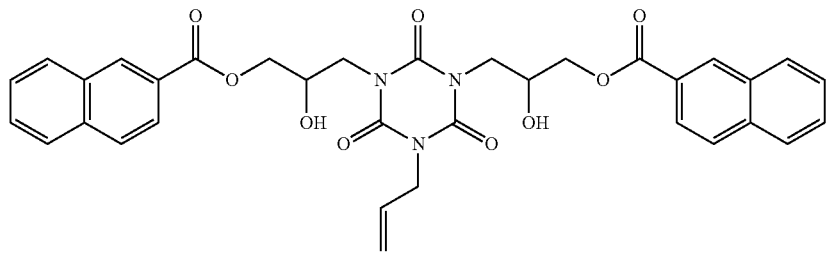
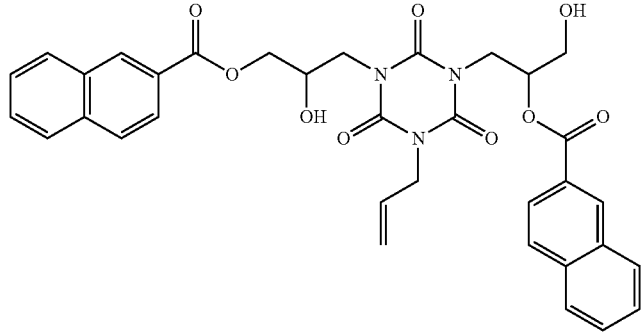

-continued
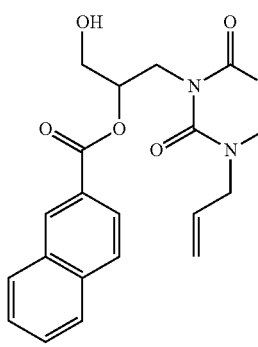
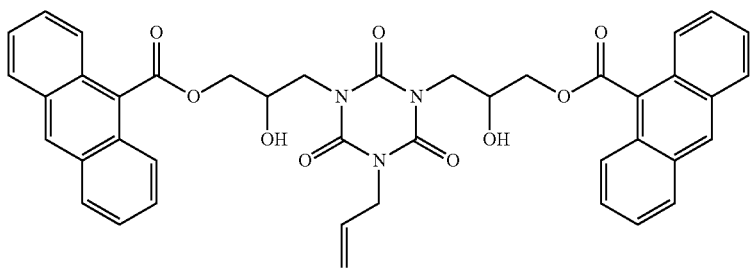
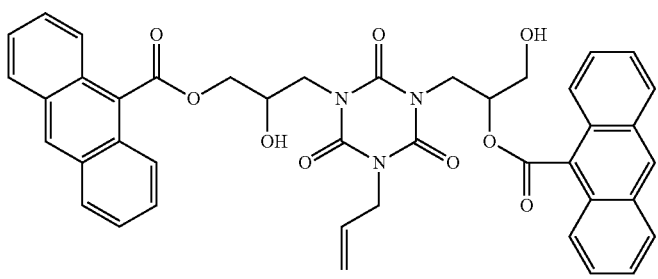
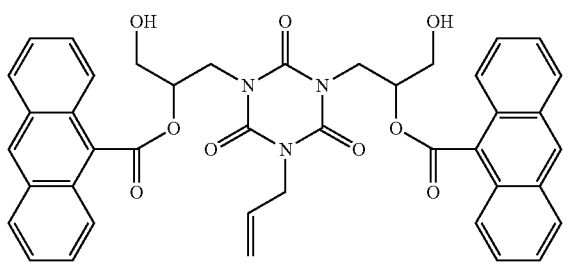
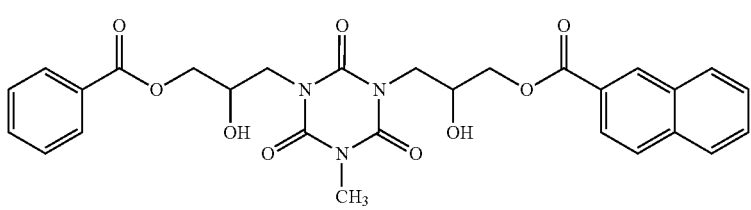
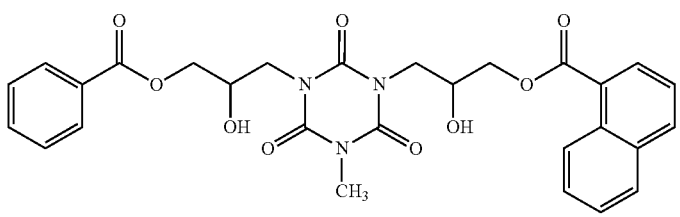

-continued
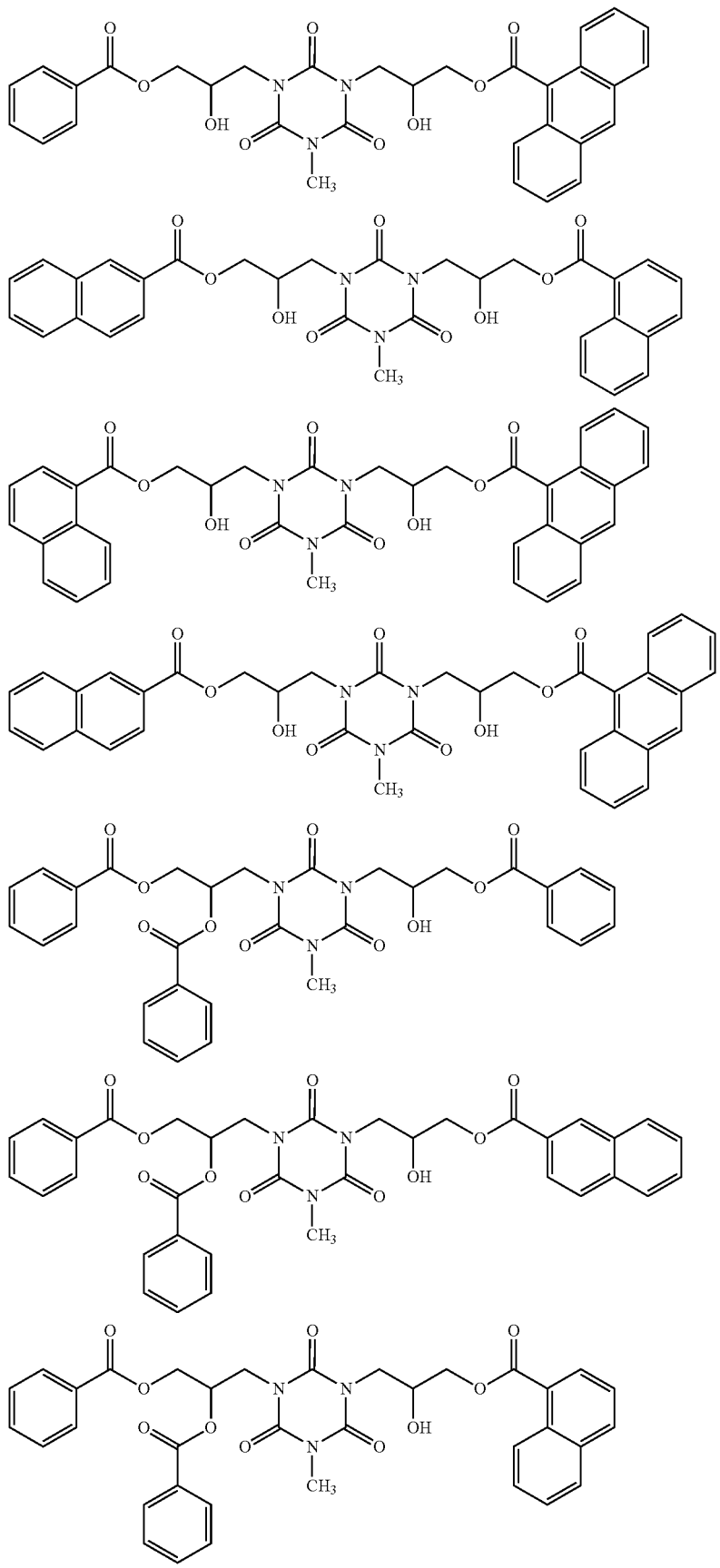

-continued
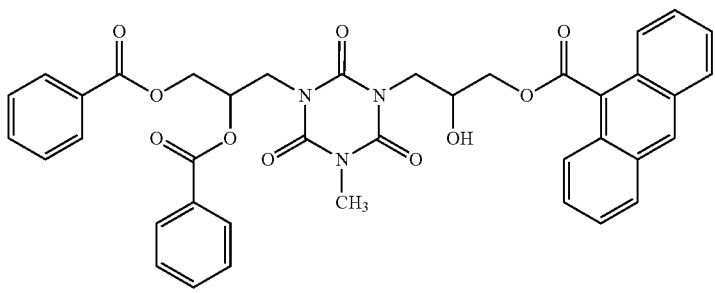
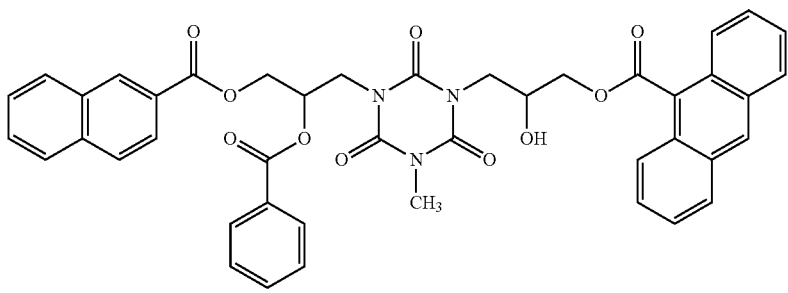
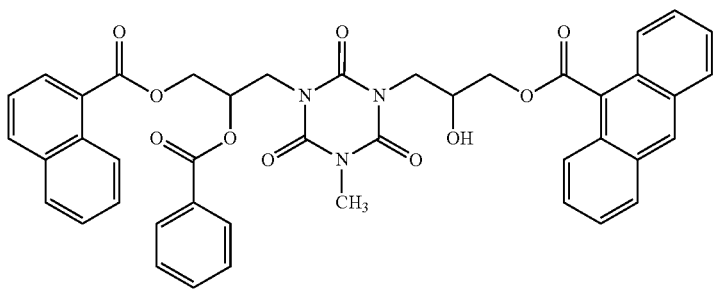
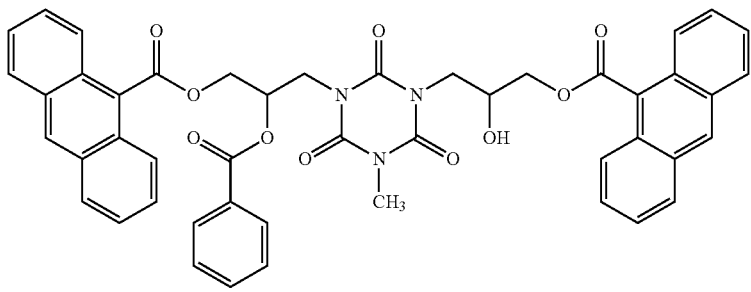
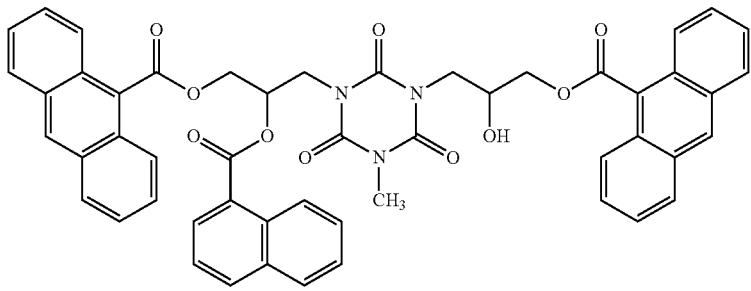

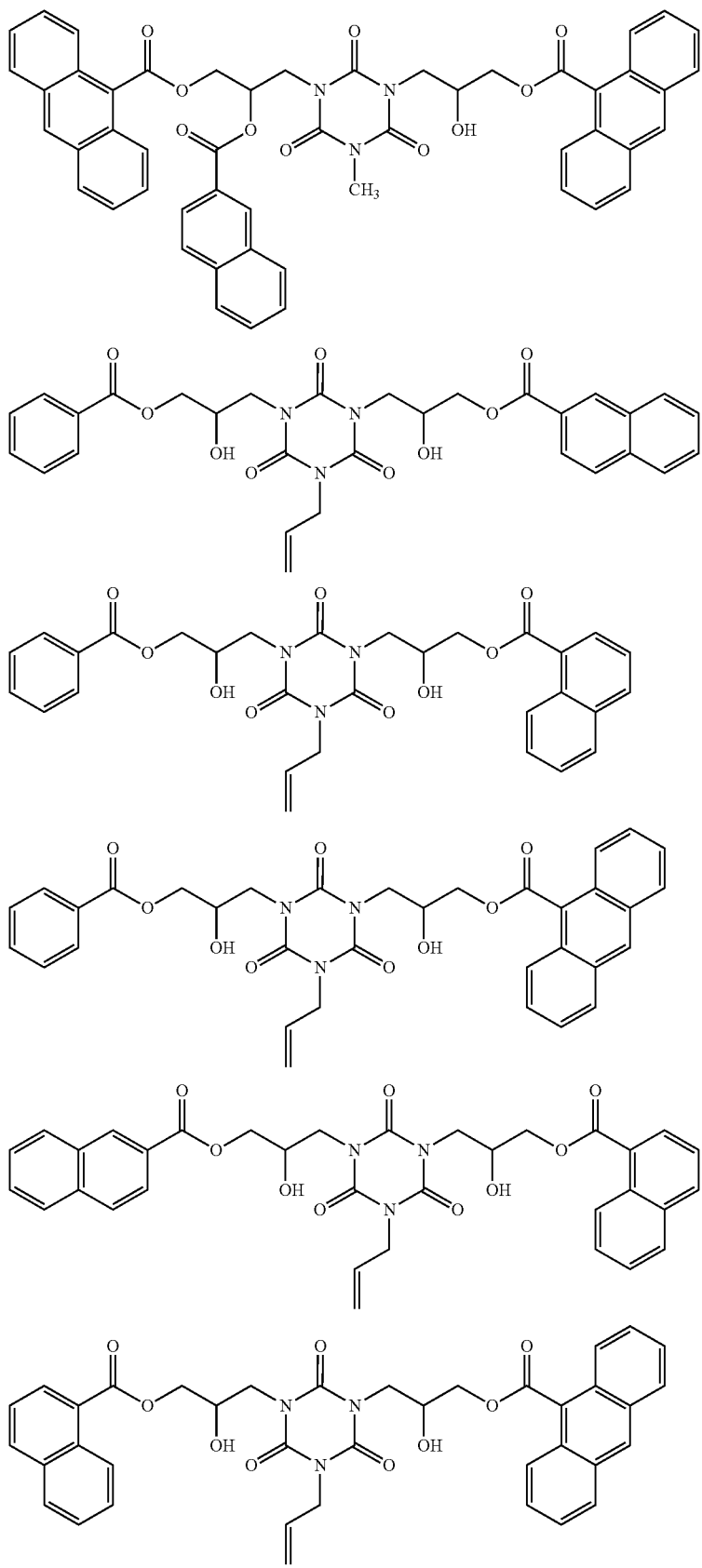

-continued
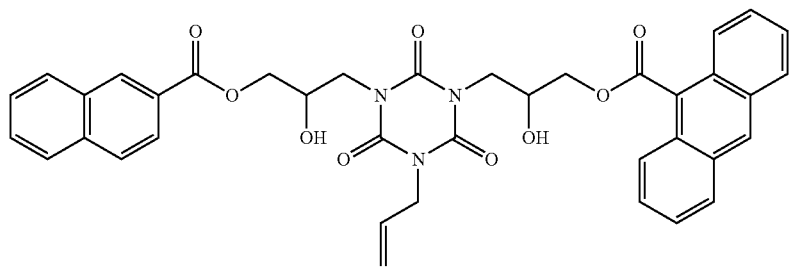
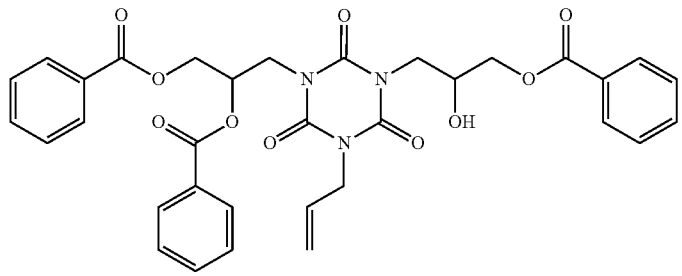
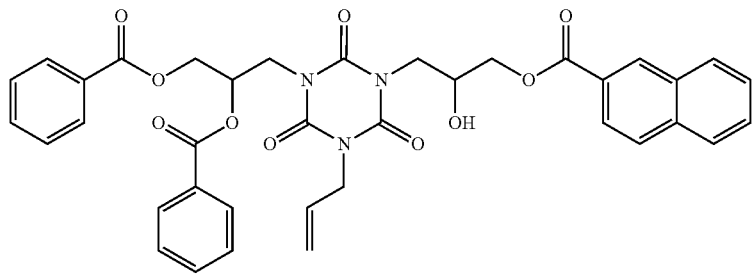
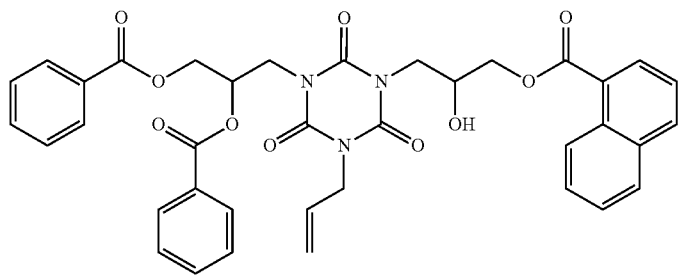
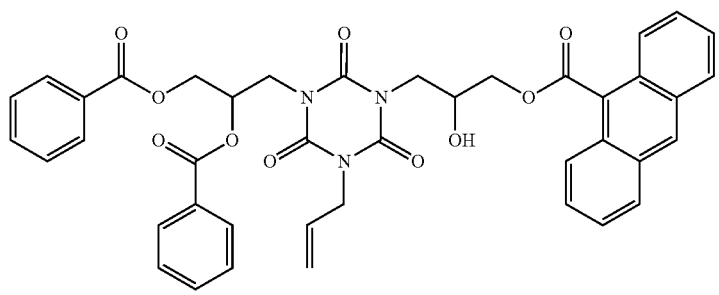
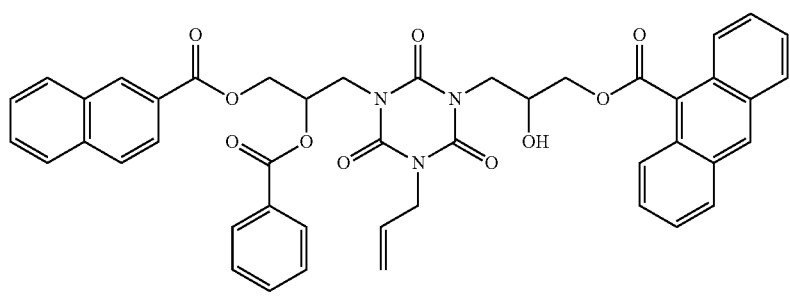

-continued
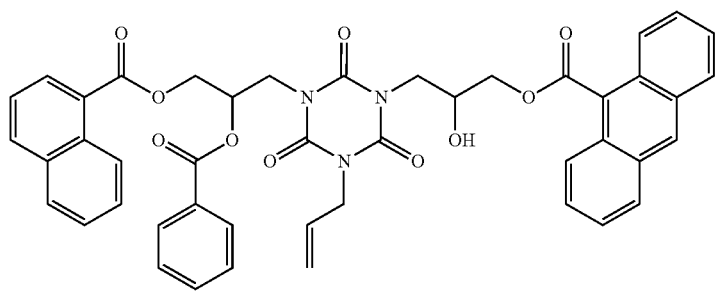
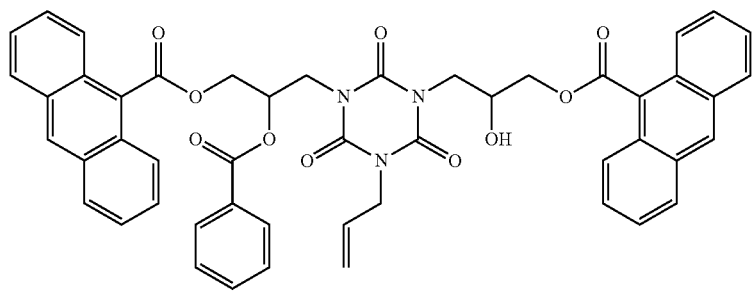
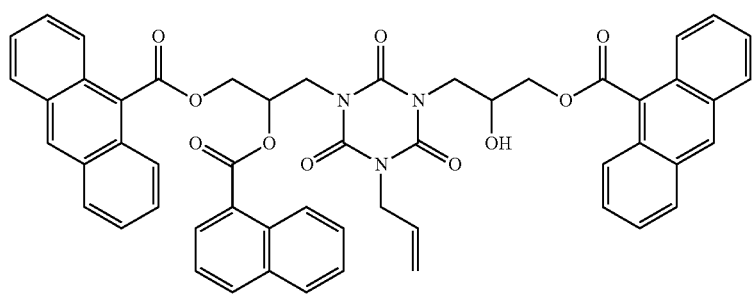
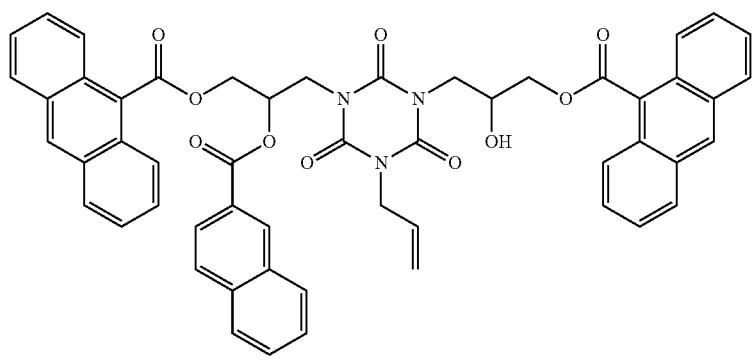
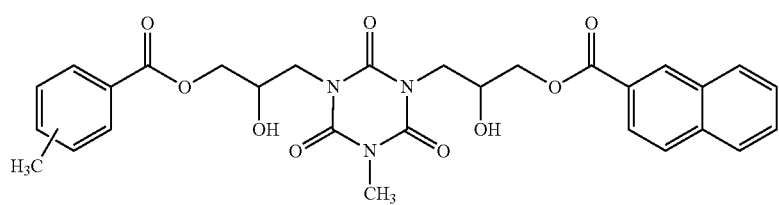
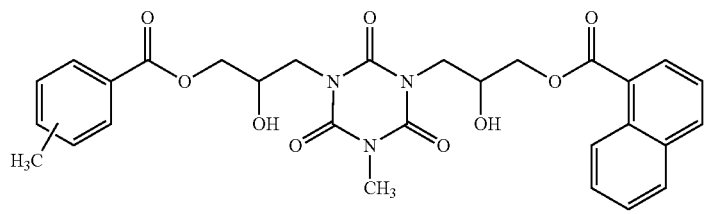

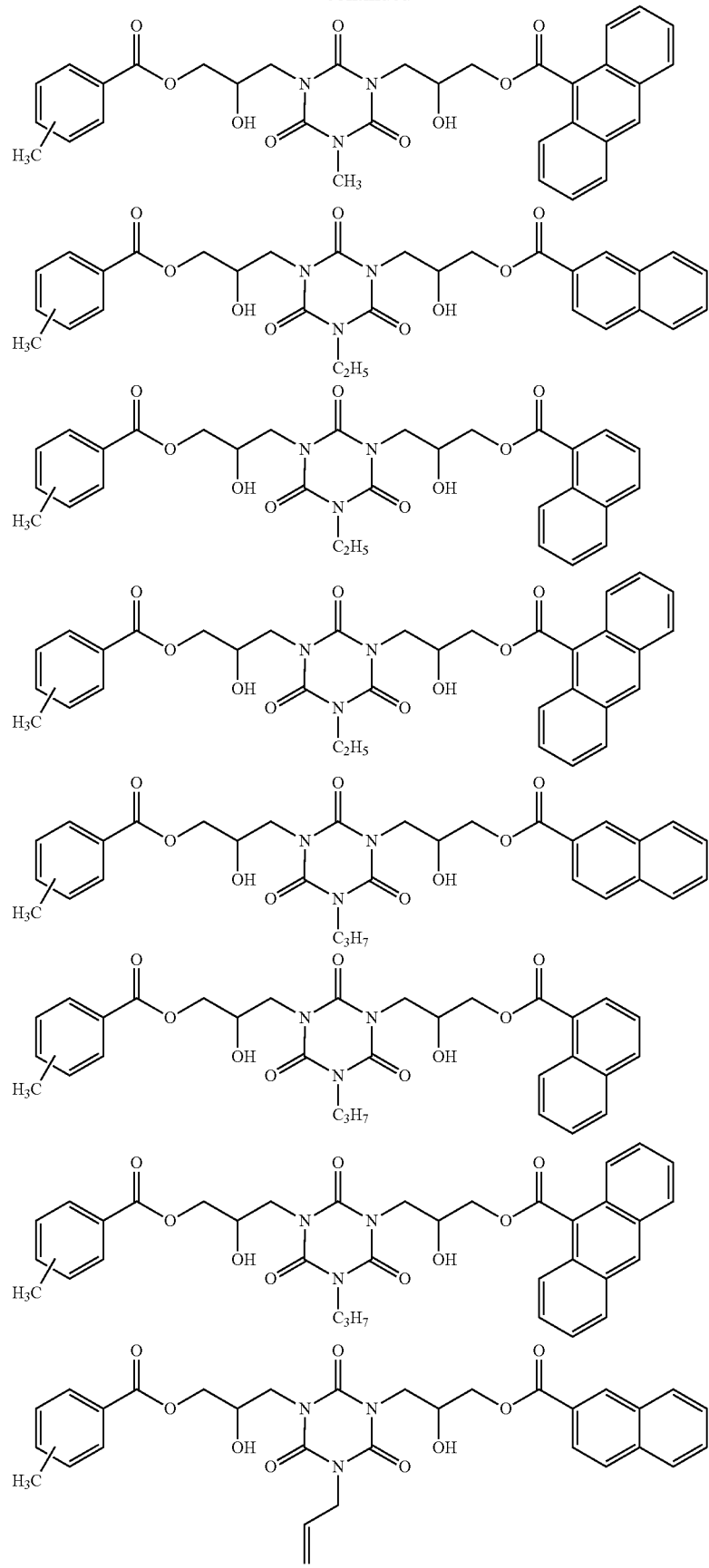

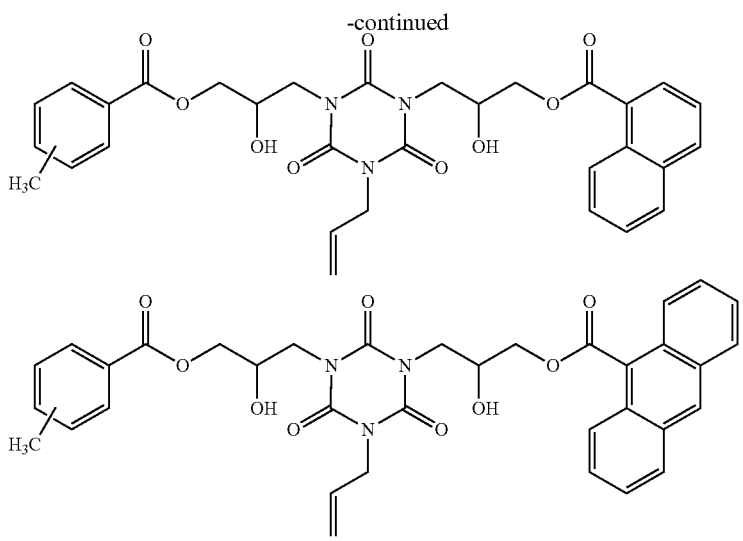

A method for obtaining the compound represented by the formula (A-1) is not particularly limited, and there may be mentioned a method in which an epoxy compound (A-0) and a carboxylic acid compound ($R^5$—COOH) are subjected to addition reaction to obtain the compound represented by the formula (A-1), as shown in the following chemical equation,

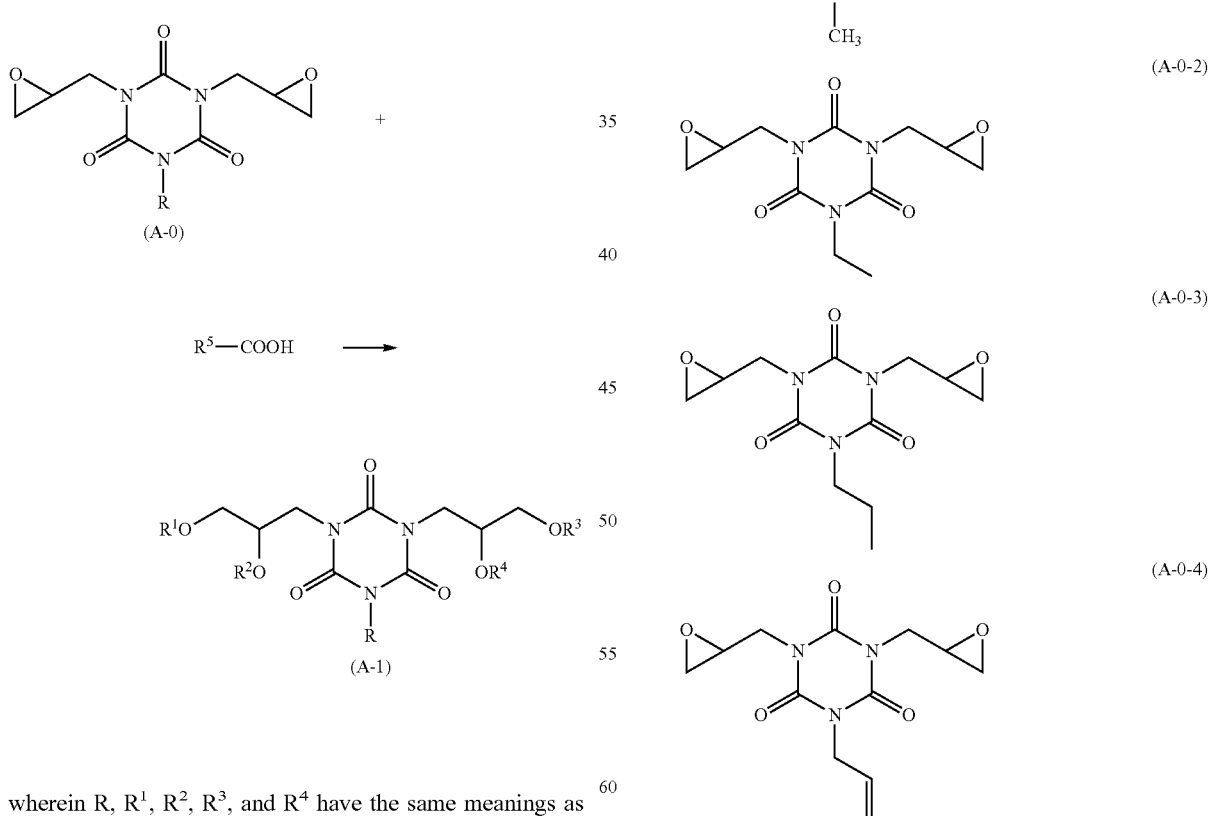

wherein R, $R^1$, $R^2$, $R^3$, and $R^4$ have the same meanings as defined above, and $R^5$ is a phenyl group, a tolyl group, a naphthyl group, or an anthracenyl group.

Examples of the epoxy compound (A-0) include the following compounds (A-0-1) to (A-0-4). Among these, the compounds (A-0-1) and (A-0-4) are preferred in view of availability of the raw material.

Examples of the carboxylic acid compound represented by $R^5$—COOH include benzoic acid, 1-toluic acid, 2-toluic acid, 3-toluic acid, 1-naphthalenecarboxylic acid, 2-naphthalenecarboxylic acid, 2-anthracenecarboxylic acid, and 9-anthracenecarboxylic acid, and these compounds may be used alone or in combination of two or more kinds thereof.

Further, as mentioned above, in the case that a compound (ultraviolet absorber) for ArF (193 nm) exposure is synthesized, benzoic acid or toluic acid is preferably used to add a benzoyl group or a toluoyl group, and in the case that a compound (ultraviolet absorber) for KrF (248 nm) exposure is synthesized, naphthalenecarboxylic acid or anthracenecarboxylic acid is preferably used to add a naphthoyl group or an anthranoyl group, by reason of absorption wavelength.

The amount of the carboxylic acid to be blended in the above-described reaction is preferably 0.3 to 2.0 mol, more preferably 0.5 to 1.5 mol, much more preferably 0.75 to 1.25 mol per 1 mol of the epoxy group in the epoxy compound.

When the amount of the carboxylic acid compound is 0.3 mol or more per 1 mol of the epoxy group, it is possible to prevent unreacted epoxy groups from remaining, which results in reduction in the amount of the ultraviolet-absorbing groups per unit weight. Thus, deterioration of the function as the antireflective film can be prevented. Also, when the amount of the carboxylic acid compound is 2.0 mol or less per 1 mol of the epoxy group, occurrence of the outgassing due to residue of the unreacted carboxylic acid compound can be prevented.

In addition, other monocarboxylic acid compounds may also be used to improve the solubility in a solvent and the compatibility with a later-described polysiloxane. Examples of the monocarboxylic acid compound include aliphatic carboxylic acids such as formic acid, acetic acid, propionic acid, palmitic acid, and stearic acid; and alicyclic carboxylic acids such as cyclohexanecarboxylic acid and norbornenecarboxylic acid. The amount of the monocarboxylic acid compounds to be blended is preferably 0.1 to 50 mol %, more preferably 1 to 30 mol % of the total blending amount of the carboxylic acid compound. If the blending amount is in such ranges, ultraviolet-absorbing properties and etching resistance are not lowered.

The compound represented by the formula (A-1) can be obtained by reaction between the epoxy compound and the carboxylic acid compound using the above-described raw materials, generally, without solvent or in a solvent, in the presence of a reaction catalyst, at room temperature or, if necessary, under cooling or heating.

Examples of the solvent used in the reaction include alcohols such as methanol, ethanol, isopropyl alcohol, butanol, ethylene glycol, propylene glycol, diethylene glycol, glycerol, methyl cellosolve, ethyl cellosolve, butyl cellosolve, and propyleneglycolmonomethyl ether; ethers such as diethyl ether, dibutyl ether, diethyleneglycoldiethyl ether, diethyleneglycoldimethyl ether, tetrahydrofuran, and 1,4-dioxane; chlorinated solvents such as methylene chloride, chloroform, dichloroethane, and trichloroethylene; hydrocarbons such as hexane, heptane, benzene, toluene, xylene, and cumene; nitriles such as acetonitrile; ketones such as acetone, ethylmethyl ketone, and isobutylmethyl ketone; esters such as ethyl acetate, n-butyl acetate, and propyleneglycolmethyl ether acetate; lactones such as γ-butyrolactone; and non-protic polar solvents such as dimethylsulfoxide, N,N-dimethylformamide, and hexamethylphosphoric triamide; and these solvents may be used alone or in combination of two or more kinds.

These solvents is preferably used with an amount in the range of 0 to 2,000 parts by mass based on 100 parts by mass of the starting material.

Examples of the reaction catalyst include quaternary ammonium salts such as benzyltriethylammonium chloride, benzyltriethylammonium bromide, benzyl-trimethylammonium chloride, tetramethylammonium chloride, tetramethylammonium bromide, tetramethylammonium iodide, tetramethylammonium hydroxide, tetraethylammonium bromide, tetrabutylammonium chloride, tetrabutylammonium bromide, tetrabutylammonium iodide, tetrabutylammonium hydrogensulfate, trioctylmethylammonium chloride, tributylbenzylammonium chloride, trimethylbenzylammonium hydroxide, N-laurylpyridinium chloride, N-lauryl-4-picolinium chloride, N-laurylpicolinium chloride, trimethylphenylammonium bromide, and N-benzylpicolinium chloride; quaternary phosphonium salts such as tetrabutylphosphonium chloride, tetrabutylphosphonium bromide, and tetraphenylphosphonium chloride; and tertiary amines such as tris[2-(2-methoxyethoxy)ethyl]-amine, tris (3,6-dioxaheptyl)amine, and tris(3,6-dioxaoctyl) amine.

The amount of the reaction catalyst to be used is in the range of 0.001 to 100% by mass, preferably 0.005 to 50% by mass based on the total amount of the starting material.

The reaction temperature is preferably about −50° C. to the boiling point of the solvent, more preferably room temperature to 150° C.

The reaction time is preferably 0.1 to 100 hours.

As the reaction method, there may be mentioned a method of collectively charging the epoxy compound, the carboxylic acid compound, and the catalyst; a method in which the epoxy compound and the carboxylic acid compound are dispersed or dissolved, and then the catalyst is collectively added thereto or the catalyst diluted with a solvent is added dropwise thereto; and a method in which the catalyst is dispersed or dissolved, and then the epoxy compound and the carboxylic acid compound are collectively added thereto or the epoxy compound and the carboxylic acid compound that have been diluted with a solvent are added dropwise thereto. After completion of the reaction, the resultant may be directly used as the ultraviolet absorber. Alternatively, the resultant may be diluted with an organic solvent and subjected to liquid separation and washing to remove the unreacted raw material, the catalyst, and so on in the system, and then the ultraviolet absorber may be collected.

The organic solvent used in this operation is not particularly limited so long as it can dissolve the compound represented by the formula (A-1) and be separated into two layers when mixed with water. Examples thereof include hydrocarbons such as hexane, heptane, benzene, toluene, and xylene; esters such as ethyl acetate, n-butyl acetate, and propyleneglycolmethyl ether acetate; ketones such as methylethyl ketone, methylamyl ketone, cyclohexanone, and methylisobutyl ketone; ethers such as diethyl ether, diisopropyl ether, methyl-t-butyl ether, and ethylcyclopentylmethyl ether; chlorinated solvents such as methylene chloride, chloroform, dichloroethane, and trichloroethylene; and mixture thereof.

Also, as the water used for washing, generally, water called deionized water or ultrapure water may be used.

The number of washing may be one or more, and preferably about 1 to 5 times because washing of 10 times or more is not worth to have full effects thereof.

In the liquid separation, washing with a basic aqueous solution may be performed to remove the unreacted carboxylic acid compound or the acidic components. Examples of the base contained in the basic aqueous solution which is used in the operation include hydroxides of alkaline metals, carbonates of alkaline metals, hydroxides of alkali earth metals, carbonates of alkali earth metals, ammonia, and organic ammonium.

Further, in the liquid separation, washing with an acidic aqueous solution may also be performed to remove the metal impurities or the basic components in the system. Examples of the acid contained in the acidic aqueous solution which is used in the operation include inorganic acids such as hydrochloric acid, hydrobromic acid, sulfuric acid, nitric acid, phosphoric acid, and heteropolyacid; and organic acids such as oxalic acid, trifluoroacetic acid, methanesulfonic acid, benzenesulfonic acid, p-toluenesulfonic acid, and trifluoromethanesulfonic acid.

The liquid separation and washing may be performed by using either or both of the basic aqueous solution and the acidic aqueous solution. In view of removal of the metal impurities, the liquid separation and washing is preferably performed by the basic aqueous solution and the acidic aqueous solution, in this order.

After the liquid separation and washing by the basic aqueous solution and/or the acidic aqueous solution, washing with neutral water may be successively performed. As the neutral water, deionized water or ultrapure water mentioned above may be used. The number of washing may be one or more, and multiple times of washing is preferred to sufficiently remove the basic compounds and the acidic compounds, but washing of 10 times or more is not worth to have full effects thereof, so that it is preferably about 1 to 5 times.

Furthermore, the reaction product after the liquid separation may be collected as a powder by concentrating and drying the solvent or subjecting the reaction product to crystallization under reduced pressured or normal pressure, or it is also possible to keep the reaction product in the state of solution with proper concentration in order to improve workability at the time of preparing a composition for forming a resist under layer film.

The concentration at this time is preferably 0.1 to 50% by mass, more preferably 0.5 to 30% by mass. If the concentration is in such ranges, there is no fear that the viscosity becomes high because of high concentration and the workability is therefore lowered, or the amount of the solvent becomes excessively large because of low concentration and it becomes uneconomical.

The final solvent used in this operation is not particularly limited so long as it can dissolve the compound represented by the formula (A-1), and illustrative examples thereof include ketones such as cyclohexanone and methyl-2-amyl ketone; alcohols such as 3-methoxybutanol, 3-methyl-3-methoxybutanol, 1-methoxy-2-propanol, and 1-ethoxy-2-propanol; ethers such as propyleneglycolmonomethyl ether, ethyleneglycolmonomethyl ether, propyleneglycolmonoethyl ether, ethyleneglycolmonoethyl ether, propyleneglycoldimethyl ether, diethyleneglycoldimethyl ether; esters such as propyleneglycolmonomethyl ether acetate, propyleneglycolmonoethyl ether acetate, ethyl lactate, ethyl pyruvate, butyl acetate, methyl 3-methoxypropionate, ethyl 3-ethoxypropionate, t-butyl acetate, t-butyl propionate, and propyleneglycolmono-t-butyl ether acetate. These may be used alone or in combination of two or more kinds.

Also, as mentioned above, the efficiency of the ultraviolet absorption can be improved by increasing the number of the ultraviolet-absorbing group (benzoyl group, toluoyl group, naphthoyl group, and anthranoyl group) in the compound represented by the formula (A-1).

The method of increasing the number of the ultraviolet-absorbing group may be exemplified by a method in which the hydroxyl group in the compound is acylated by using an acylating reagent, as shown in the following chemical equation,

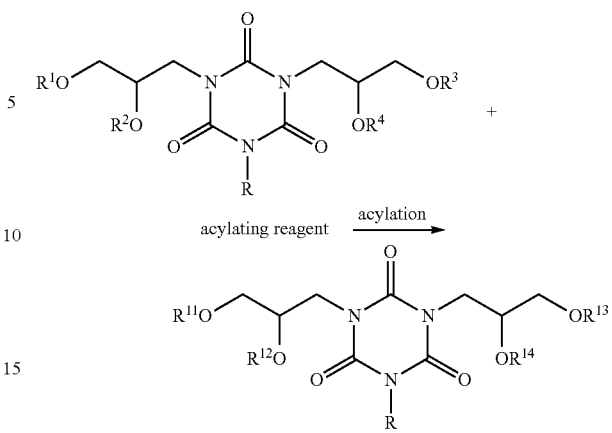

wherein R, $R^1$, $R^2$, $R^3$, and $R^4$ have the same meanings as defined above, and $R^{11}$, $R^{12}$, $R^{23}$, and $R^{14}$ may be the same or different, and each represent a hydrogen atom, a benzoyl group, a toluoyl group, a naphthoyl group, or an anthranoyl group, with the provisos that three or more of $R^{11}$, $R^{12}$, $R^{13}$, and $R^{14}$ are each selected from a benzoyl group, a toluoyl group, a naphthoyl group, and an anthranoyl group.

The acylation can be carried out by a known method. The acylating reagent used in the method is preferably an acid chloride or an acid anhydride corresponding to benzoic acid, 1-toluic acid, 2-toluic acid, 3-toluic acid, 1-naphthalenecarboxylic acid, 2-naphthalenecarboxylic acid, 2-anthracenecarboxylic acid, 9-anthracenecarboxylic acid, etc.

When an acid chloride is used, it is preferred that the compound that is used as the starting material, the acid chloride, and a base such as triethylamine, pyridine, and 4-dimethylaminopyridine be added sequentially or simultaneously without solvent or in a solvent such as methylene chloride, acetonitrile, toluene, hexane to perform the reaction, if necessary, under heating or cooling.

Meanwhile when an acid anhydride is used, it is preferred that the compound that is used as the starting material, the acid anhydride, and a base such as triethylamine, pyridine, and 4-dimethylaminopyridine be added sequentially or simultaneously in a solvent such as toluene to perform the reaction, if necessary, under heating or cooling.

The resulting product may be purified by water-washing or the like, and collected as a powder or a solution. Example of the final solvent used at this time include the same as exemplified above. The concentration thereof is preferably 0.1 to 50% by mass, more preferably 0.5 to 30% by mass.

When the ultraviolet absorber containing the compound represented by the formula (A-1) as mentioned above is added to a composition for forming a resist under layer film, the ultraviolet absorber can suppress reflection by adsorbing ultraviolet rays particularly in lithography process by an ultraviolet laser such as ArF laser and KrF laser, and can improve a pattern profile without adverse effects on dry etching mask properties and adhesiveness to a resist pattern formed on the resist under layer film.

<Composition for Forming a Resist Under Layer Film>

Also, the present invention provides a composition for forming a resist under layer film which contains the ultraviolet absorber of the present invention and a polysiloxane.

In the composition for forming a resist under layer film of the present invention, the ultraviolet absorber of the present invention can be used alone or in combination with two or more kinds thereof.

The amount of the ultraviolet absorber to be added is preferably 0.01 to 50 parts by mass, more preferably 0.1 to 40 parts by mass, based on 100 parts by mass of the base polymer (e.g. a later-described polysiloxane).

[Polysiloxane]

The polysiloxane contained in the composition for forming a resist under layer film of the present invention preferably contains one or more members selected from a compound represented by the formula (B-1), a hydrolysate of the compound, a condensate of the compound, and a hydrolysis condensate of the compound,

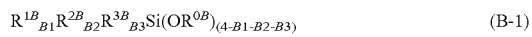

wherein $R^{OB}$ represents a hydrocarbon group having 1 to 6 carbon atoms; $R^{1B}$, $R^{2B}$, and $R^{3B}$ each represent a hydrogen atom or a monovalent organic group; and B1, B2, and B3 are each 0 or 1, and satisfy $0 \leq B1+B2+B3 \leq 3$.

A hydrolysable silicon compound (alkoxysilane) represented by the formula (B-1) used as a raw material (stating material) of the polysiloxane can be exemplified by the following.

Illustrative examples of tetraalkoxysilane include tetramethoxysilane, tetraethoxysilane, tetrapropoxy-silane, tetraisopropoxysilane, etc.

Illustrative examples of trialkoxysilane include trimethoxysilane, triethoxysilane, tripropoxysilane, triisopropoxysilane, methyltrimethoxysilane, methyl-triethoxysilane, methyltripropoxysilane, methyl-triisopropoxysilane, ethyltrimethoxysilane, ethyl-triethoxysilane, ethyltripropoxysilane, ethyl-triisopropoxysilane, vinyltrimethoxysilane, vinyl-triethoxysilane, vinyltripropoxysilane, vinyl-triisopropoxysilane, propyltrimethoxysilane, propyl-triethoxysilane, propyltripropoxysilane, propyl-triisopropoxysilane, isopropyltrimethoxysilane, isopropyltriethoxysilane, isopropyltripropoxysilane, isopropyltriisopropoxysilane, butyltrimethoxysilane, butyltriethoxysilane, butyltripropoxysilane, butyl-triisopropoxysilane, s-butyltrimethoxysilane, s-butyltriethoxysilane, s-butyltripropoxysilane, s-butyl-triisopropoxysilane, t-butyltrimethoxysilane, t-butyltriethoxysilane, t-butyltripropoxysilane, t-butyl-triisopropoxysilane, cyclopropyltrimethoxysilane, cyclopropyltriethoxysilane, cyclopropyltripropoxysilane, cyclopropyltriisopropoxysilane, cyclobutyltrimethoxy-silane, cyclobutyltriethoxysilane, cyclobutyltripropoxy-silane, cyclobutyltriisopropoxysilane, cyclopentyl-trimethoxysilane, cyclopentyltriethoxysilane, cyclopentyltripropoxysilane, cyclopentyltriisopropoxy-silane, cyclohexyltrimethoxysilane, cyclohexyltriethoxy-silane, cyclohexyltripropoxysilane, cyclohexyl-triisopropoxysilane, cyclohexenyltrimethoxysilane, cyclohexenyltriethoxysilane, cyclohexenyltripropoxy-silane, cyclohexenyltriisopropoxysilane, cyclohexenylethyltrimethoxysilane, cyclohexenylethyl-triethoxysilane, cyclohexenylethyltripropoxysilane, cyclohexenylethyltriisopropoxysilane, cyclooctyltrimethoxysilane, cyclooctyltriethoxysilane, cyclooctyltripropoxysilane, cyclooctyltriisopropoxysilane, cyclopentadienylpropyltrimethoxysilane, cyclopentadienylpropyltriethoxysilane, cyclopentadienylpropyltripropoxysilane, cyclopentadienylpropyltriisopropoxysilane, bicycloheptenyltrimethoxysilane, bicycloheptenyl-triethoxysilane, bicycloheptenyltripropoxysilane, bicycloheptenyltriisopropoxysilane, bicycloheptyltrimethoxysilane, bicycloheptyltriethoxysilane, bicycloheptyltripropoxysilane, bicycloheptyl-triisopropoxysilane, adamantyltrimethoxysilane, adamantyltriethoxysilane, adamantyltripropoxysilane, adamantyltriisopropoxysilane, phenyltrimethoxysilane, phenyltriethoxysilane, phenyltripropoxysilane, phenyl-triisopropoxysilane, benzyltrimethoxysilane, benzyl-triethoxysilane, benzyltripropoxysilane, benzyl-triisopropoxysilane, tolyltrimethoxysilane, tolyl-triethoxysilane, tolyltripropoxysilane, tolyl-triisopropoxysilane, anisyltrimethoxysilane, anisyl-triethoxysilane, anisyltripropoxysilane, anisyl-triisopropoxysilane, phenethyltrimethoxysilane, phenethyltriethoxysilane, phenethyltripropoxysilane, phenethyltriisopropoxysilane, naphthyltrimethoxysilane, naphthyltriethoxysilane, naphthyltripropoxysilane, naphthyltriisopropoxysilane, etc.

Illustrative examples of dialkoxysilane include dimethyldimethoxysilane, dimethyldiethoxysilane, methylethyldimethoxysilane, methylethyldiethoxysilane, dimethyldipropoxysilane, dimethyldiisopropoxysilane, diethyldimethoxysilane, diethyldiethoxysilane, diethyldipropoxysilane, diethyldiisopropoxysilane, dipropyl-dimethoxysilane, dipropyldiethoxysilane, dipropyl-dipropoxysilane, dipropyldiisopropoxysilane, diisopropyldimethoxysilane, diisopropyldiethoxysilane, diisopropyldipropoxysilane, diisopropyldiisopropoxy-silane, dibutyldimethoxysilane, dibutyldiethoxysilane, dibutyldipropoxysilane, dibutyldiisopropoxysilane, di-s-butyldimethoxysilane, di-s-butyldiethoxysilane, di-s-butyldipropoxysilane, di-s-butyldiisopropoxysilane, di-t-butyldimethoxysilane, di-t-butyldiethoxysilane, di-t-butyldipropoxysilane, di-t-butyldiisopropoxysilane, dicyclopropyldimethoxysilane, dicyclopropyldiethoxy-silane, dicyclopropyldipropoxysilane, dicyclopropyl-diisopropoxysilane, dicyclobutyldimethoxysilane, dicyclobutyldiethoxysilane, dicyclobutyldipropoxysilane, dicyclobutyldiisopropoxysilane, dicyclopentyldimethoxy-silane, dicyclopentyldiethoxysilane, dicyclopentyldipropoxysilane, dicyclopentyldiisopropoxysilane, dicyclohexyldimethoxysilane, dicyclohexyldiethoxysilane, dicyclohexyldipropoxysilane, dicyclohexyldiisopropoxy-silane, dicyclohexenyldimethoxysilane, dicyclohexenyl-diethoxysilane, dicyclohexenyldipropoxysilane, dicyclohexenyldiisopropoxysilane, dicyclohexenylethyl-dimethoxysilane, dicyclohexenylethyldiethoxysilane, dicyclohexenylethyldipropoxysilane, dicyclohexenylethyldiisopropoxysilane, dicyclooctyldimethoxysilane, dicyclooctyldiethoxysilane, dicyclooctyldipropoxysilane, dicyclooctyldiisopropoxysilane, dicyclopentadienylpropyldimethoxysilane, dicyclopentadienylpropyldiethoxysilane, dicyclopentadienylpropyldipropoxysilane, dicyclopentadienylpropyldiisopropoxysilane, bis(bicycloheptenyl)dimethoxysilane, bis(bicycloheptenyl)diethoxysilane, bis(bicycloheptenyl)dipropoxysilane, bis(bicycloheptenyl)diisopropoxysilane, bis(bicycloheptyl)dimethoxysilane, bis(bicycloheptyl)-diethoxysilane, bis(bicycloheptyl)dipropoxysilane, bis(bicycloheptyl)diisopropoxysilane, diadamantyl-dimethoxysilane, diadamantyldiethoxysilane, diadamantyldipropoxysilane, diadamantyldiisopropoxysilane, diphenyldimethoxysilane, diphenyldiethoxysilane, methylphenyldimethoxysilane, methylphenyldiethoxysilane, diphenyldipropoxysilane, diphenyldiisopropoxysilane, etc.

Illustrative examples of monoalkoxysilane include trimethylmethoxysilane, trimethylethoxysilane, dimethylethylmethoxysilane, dimethylethylethoxysilane, dimethylphenylmethoxysilane, dimethylphenylethoxysilane, dimethylbenzylmethoxysilane, dimethylbenzylethoxysilane, dimethylphenethylmethoxysilane, dimethylphenethylethoxy-silane, etc.

Other examples of the compound represented by the formula (B-1) include those having the following structures whose silicon is bonded to one to three methoxy groups, ethoxy groups, propoxy groups, butoxy groups, pentoxy groups, cyclopentoxy groups, hexyloxy groups, cyclohexyloxy groups, and phenoxy groups as hydrolysable group, $OR^{OB}$.
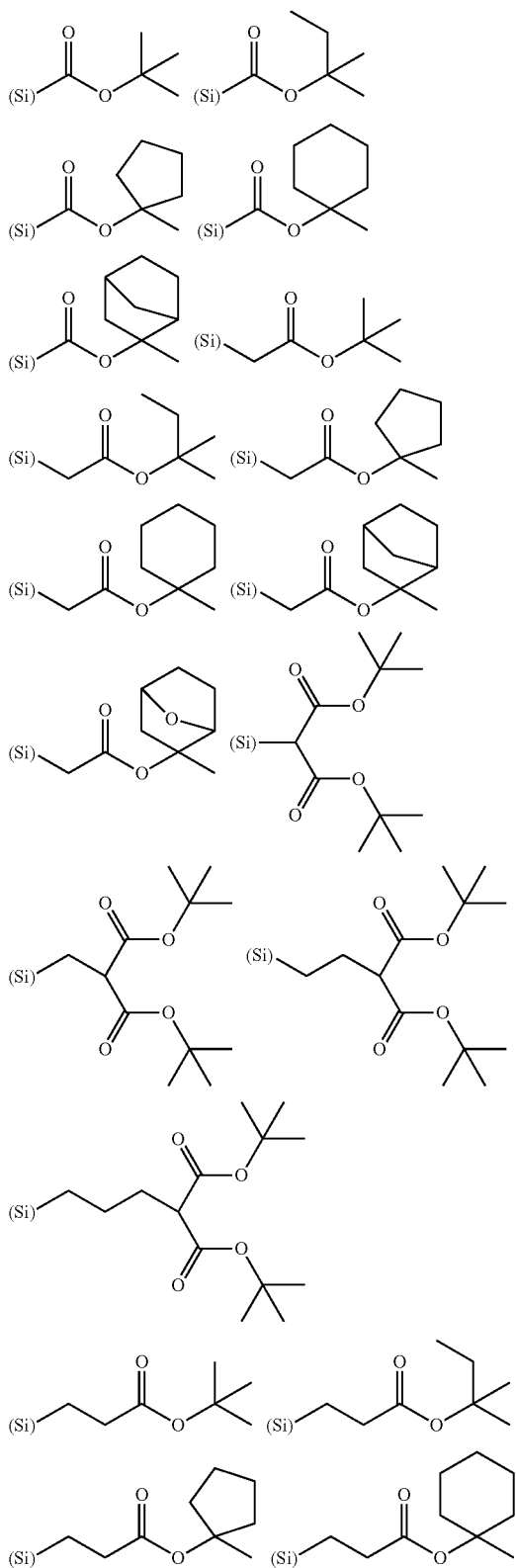
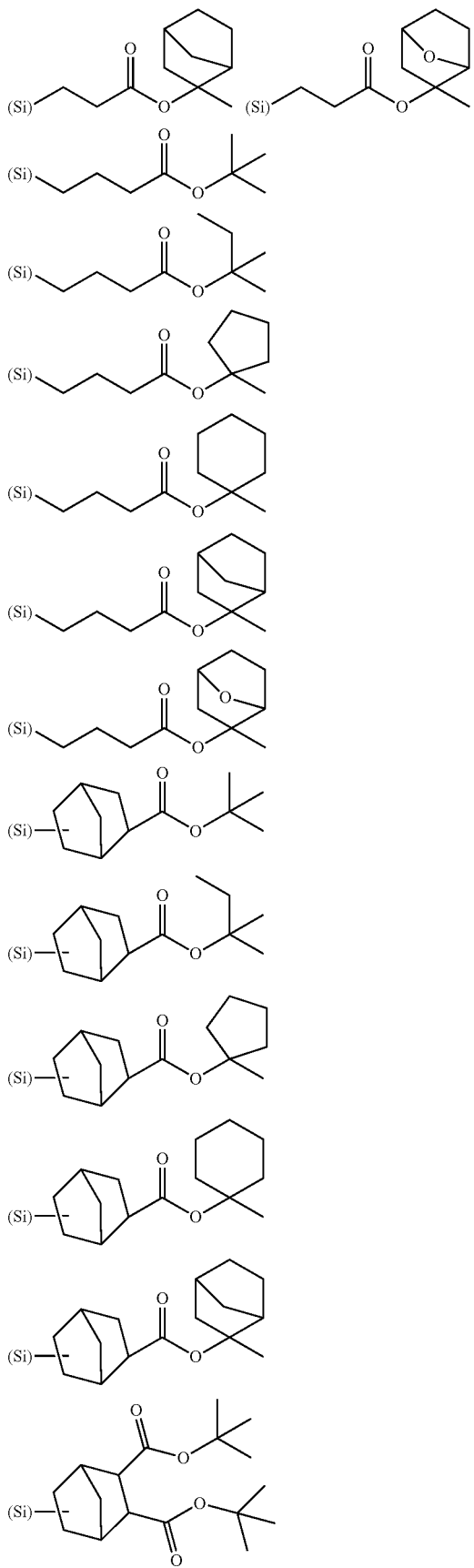

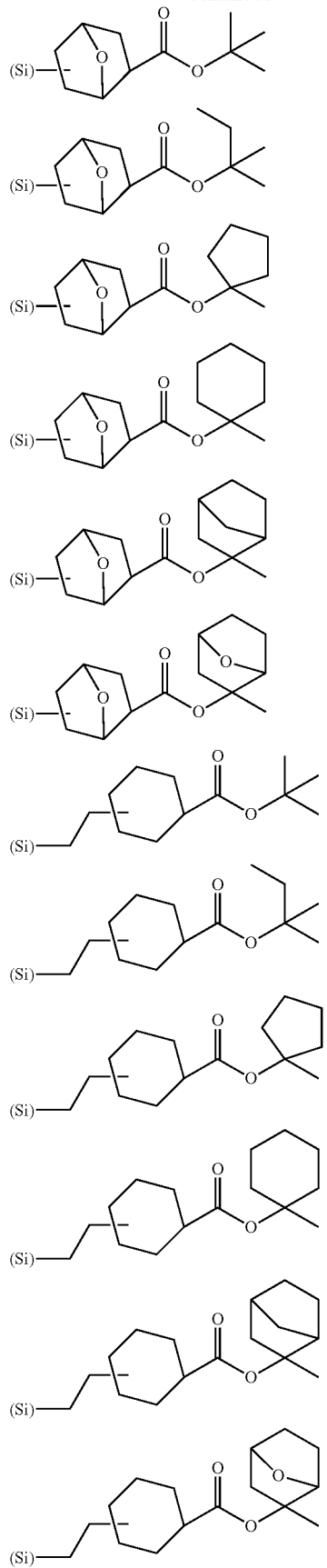
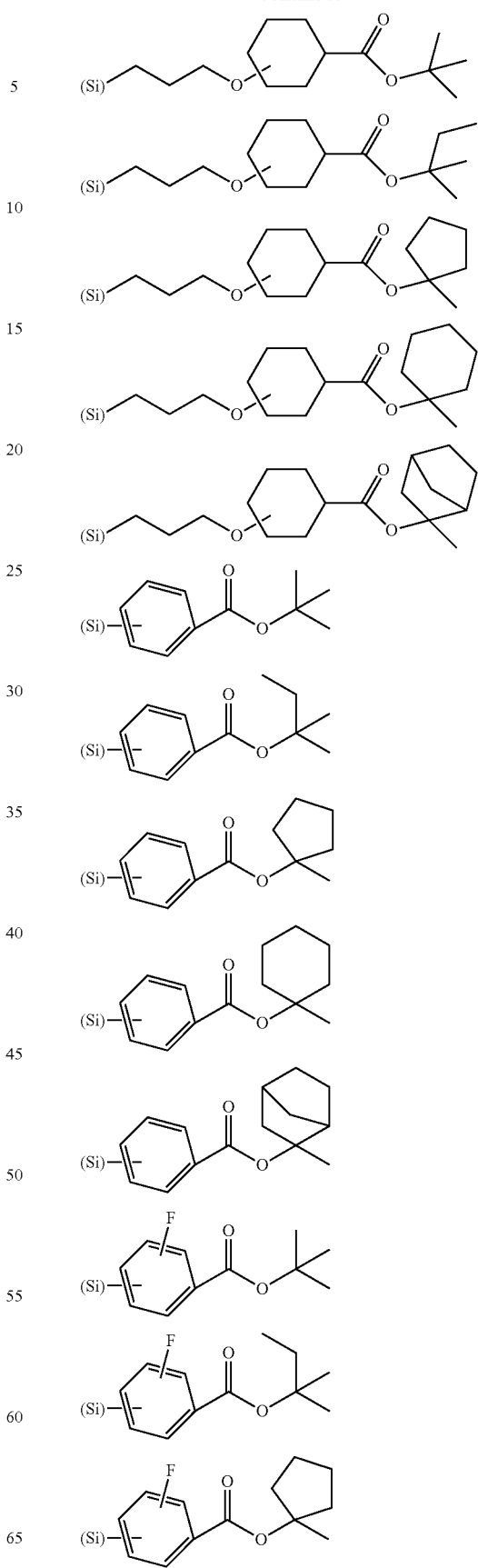

-continued
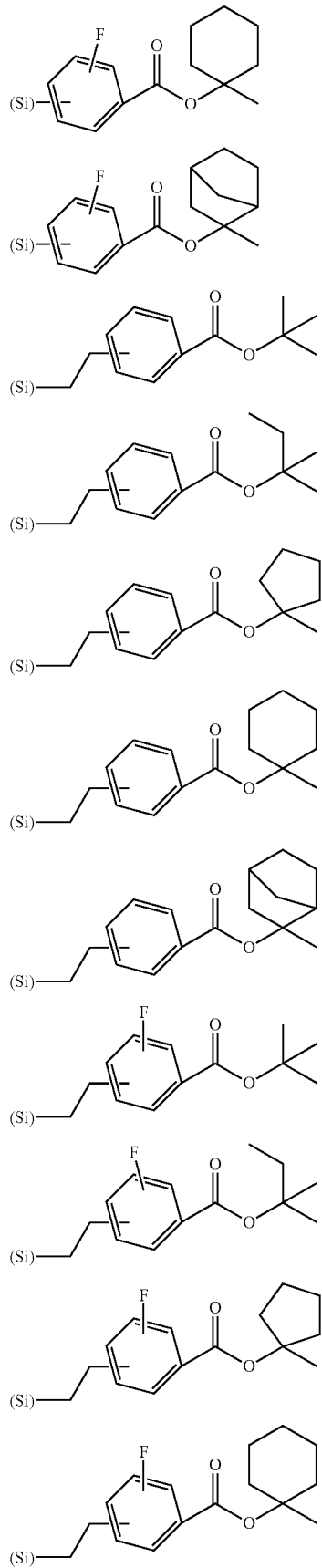
-continued
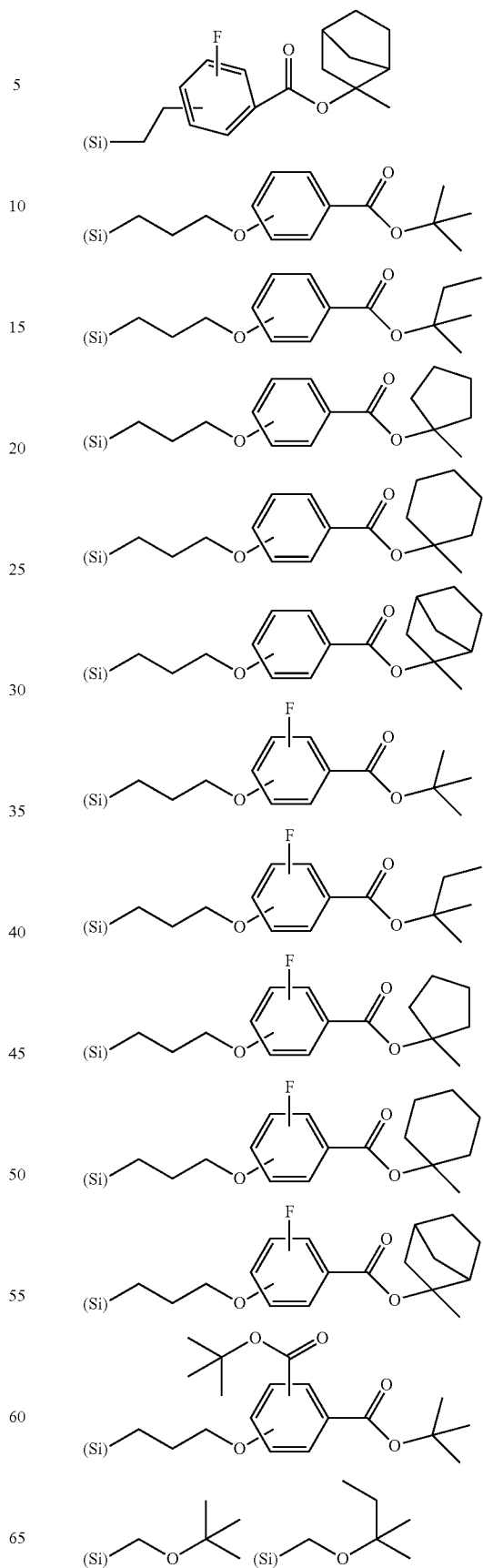

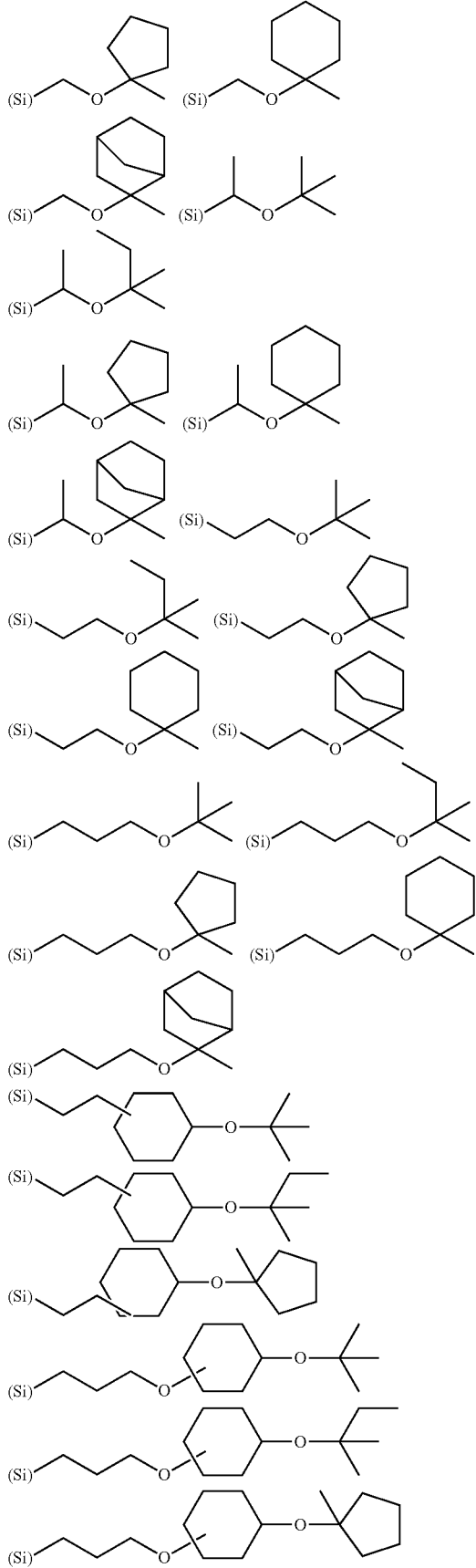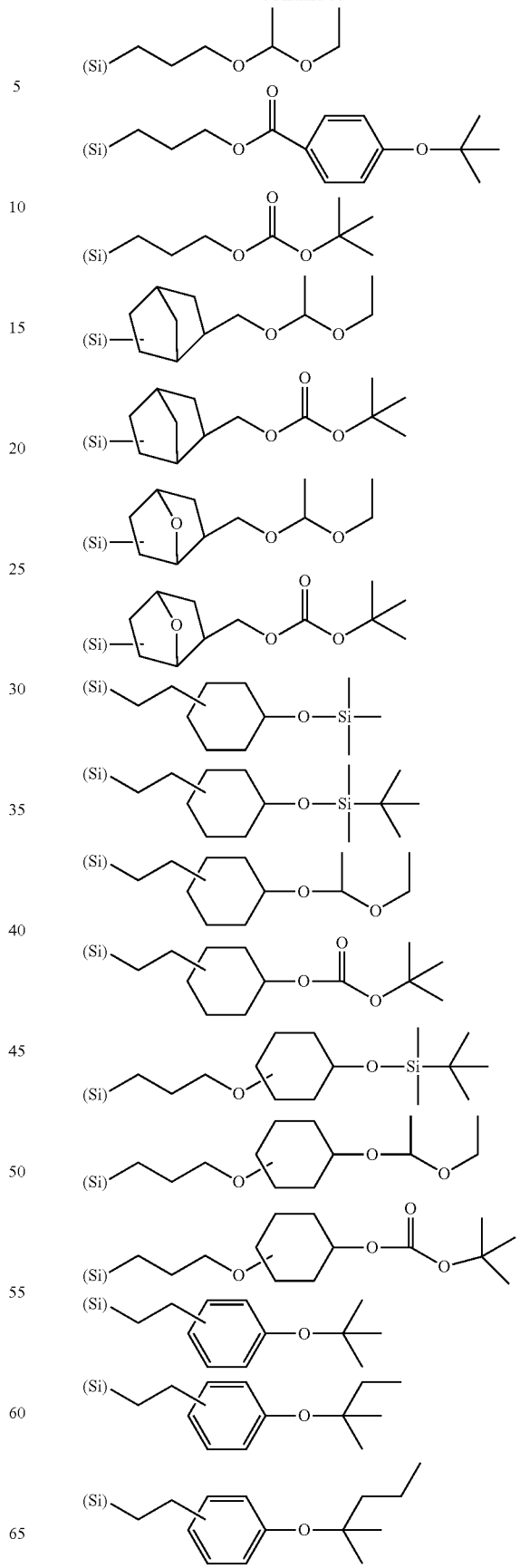

-continued
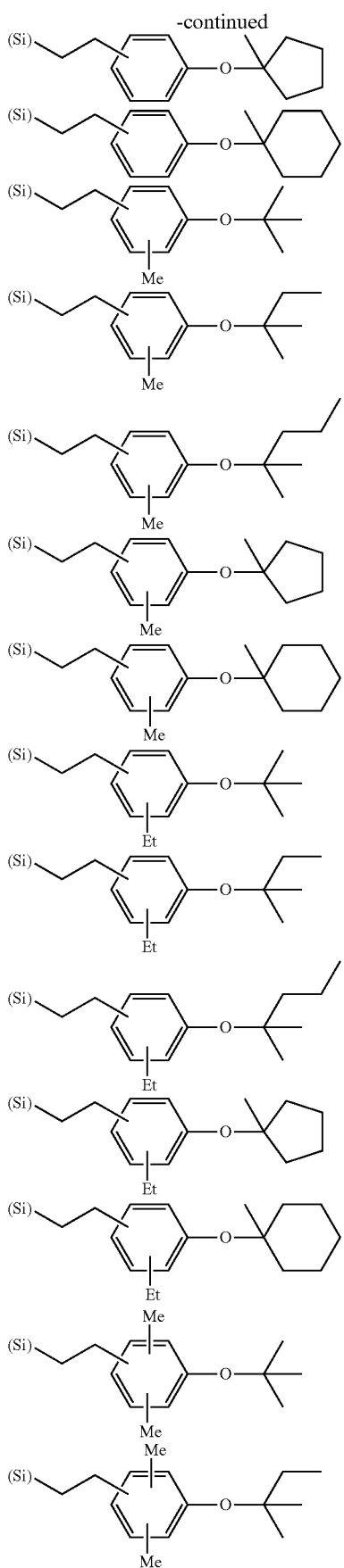
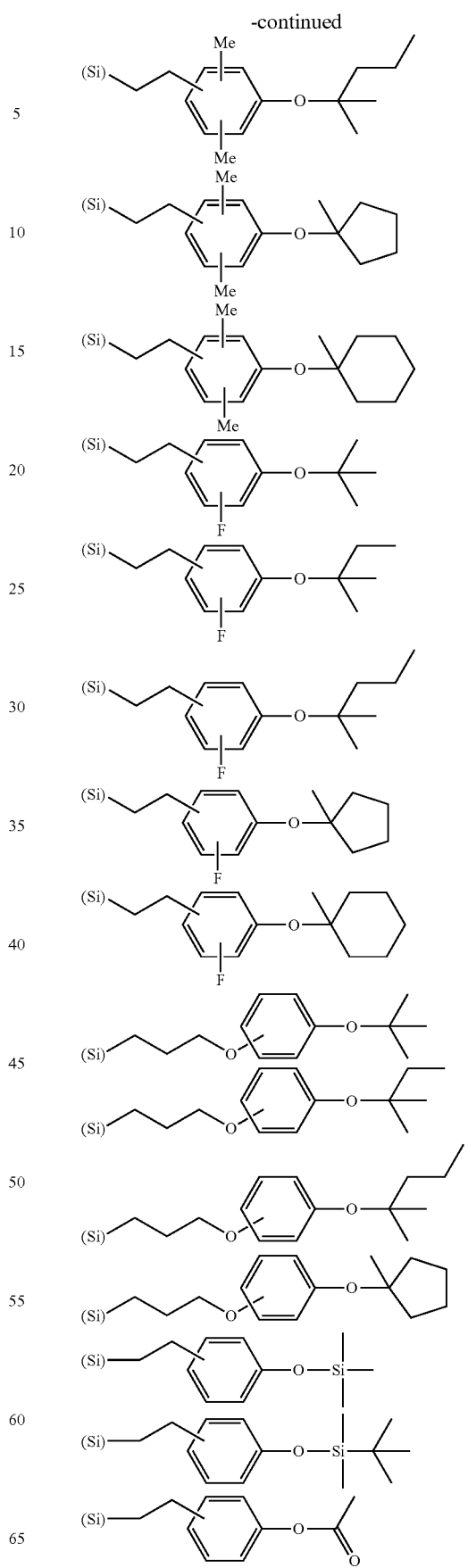

49
-continued
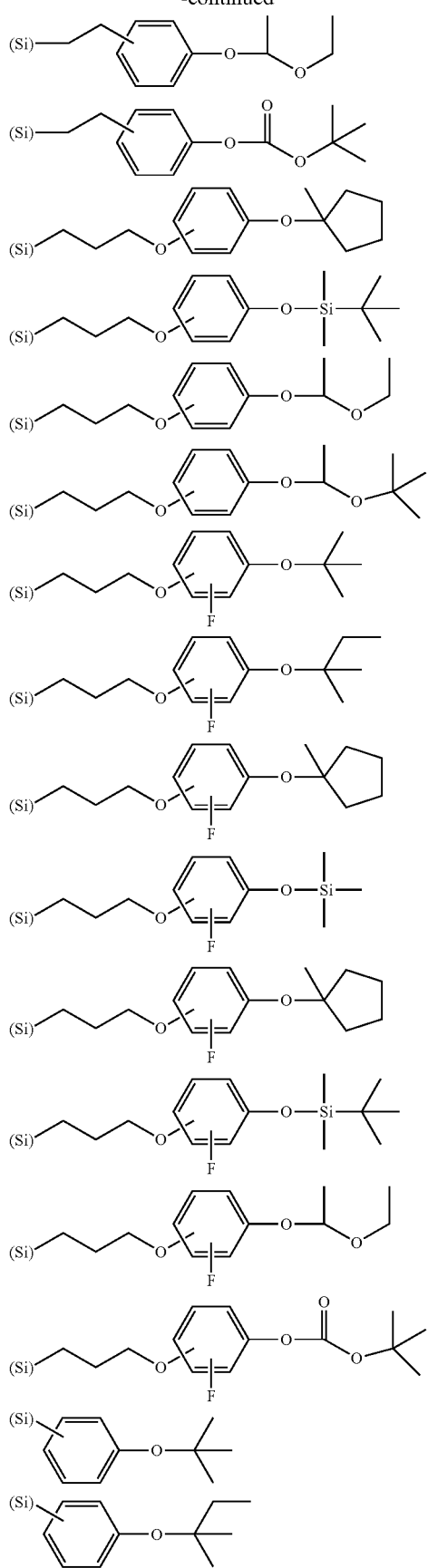
50
-continued
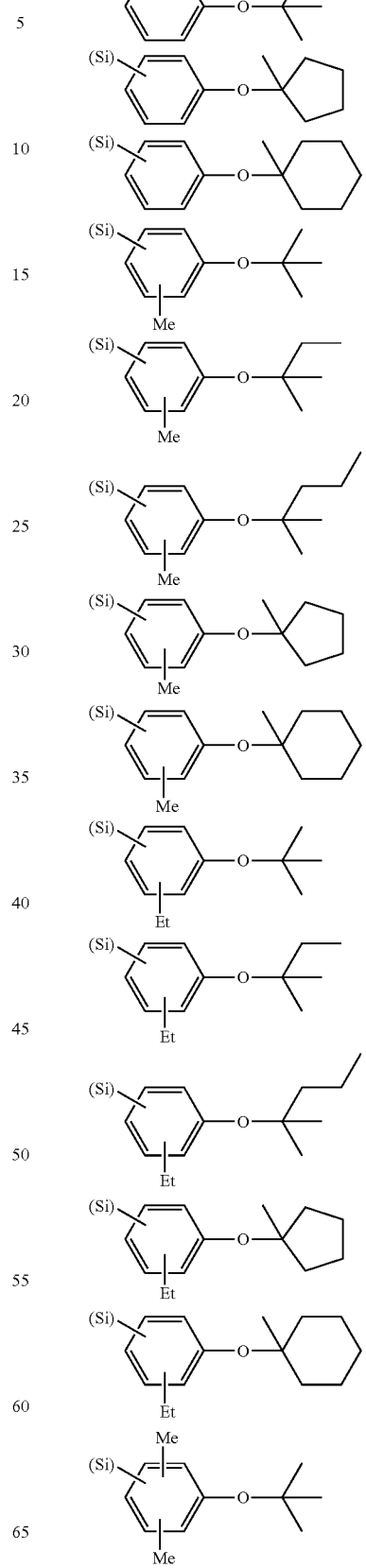

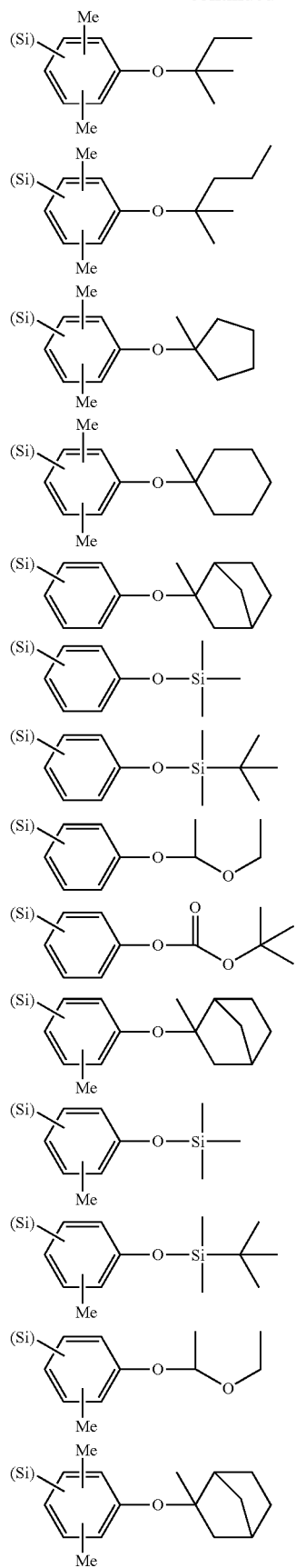
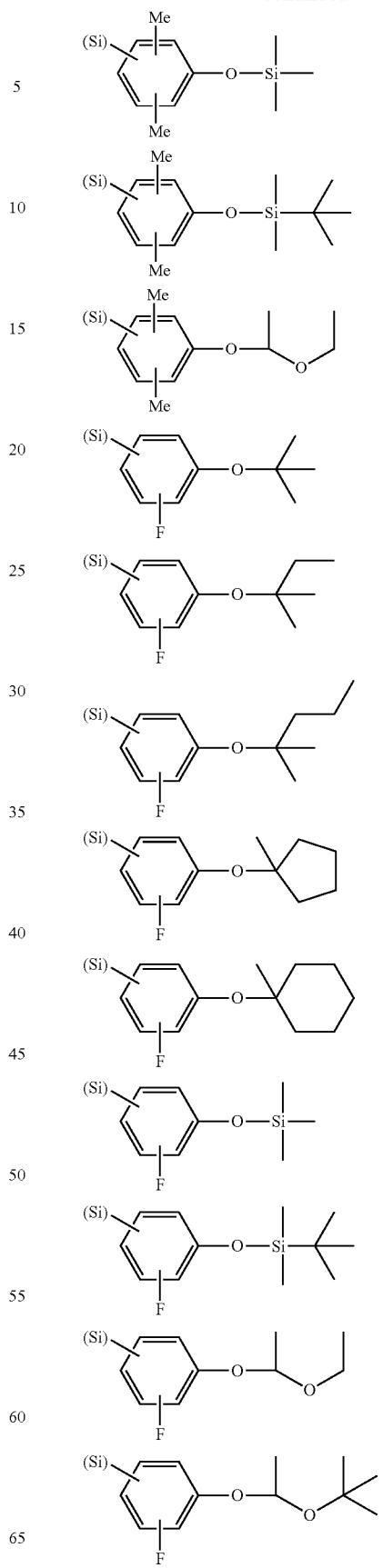

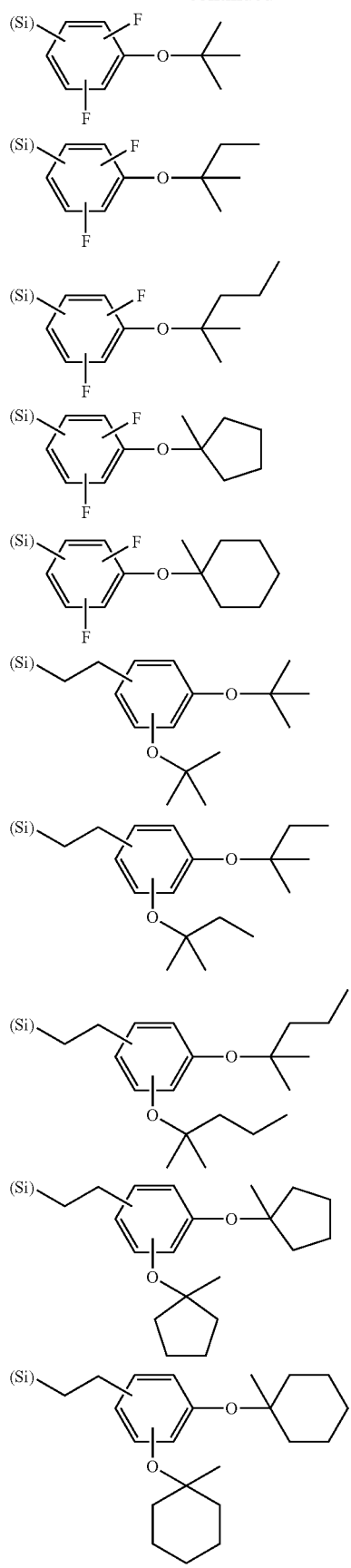
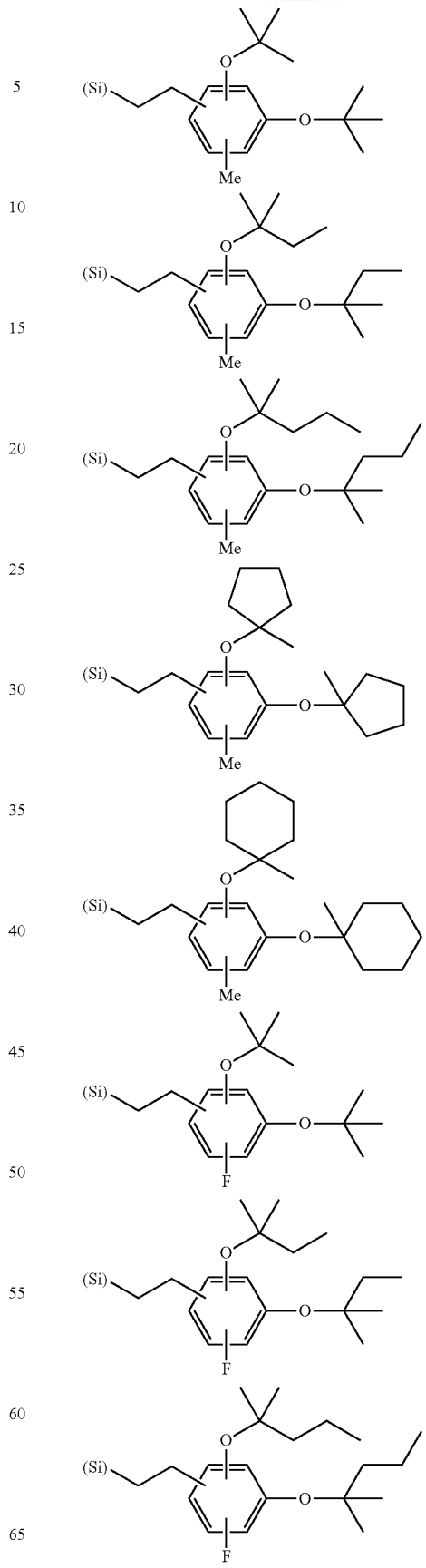

-continued
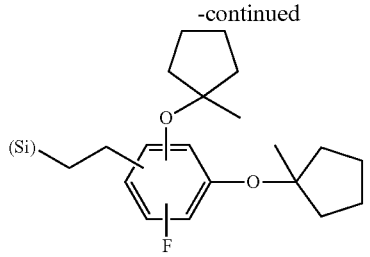
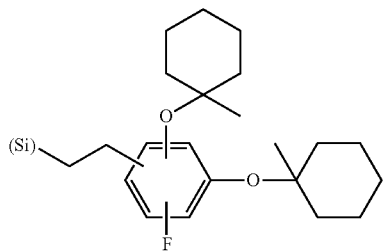
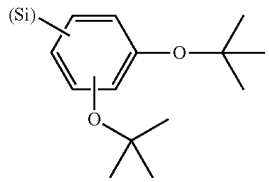
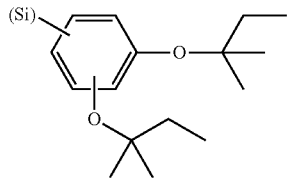
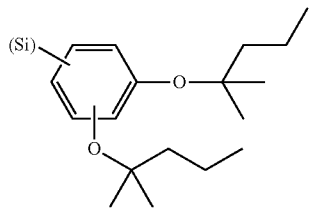
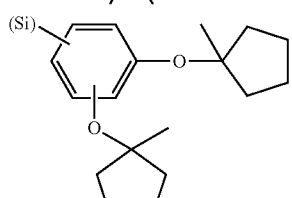
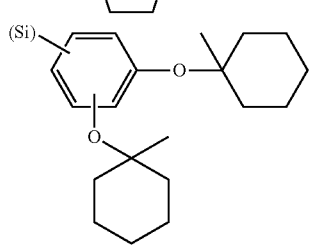
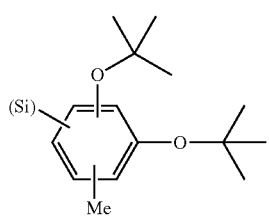
-continued
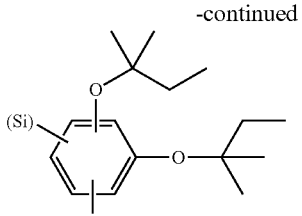
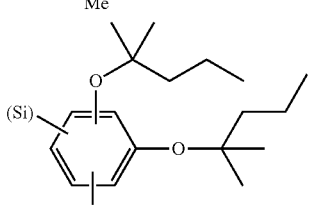
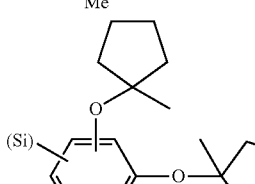
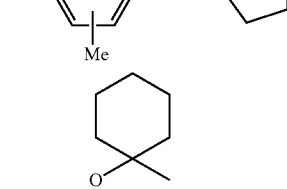
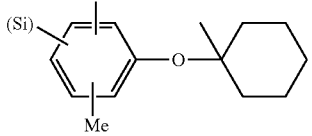
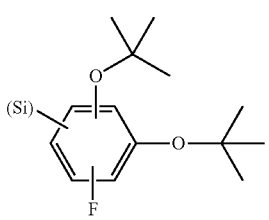
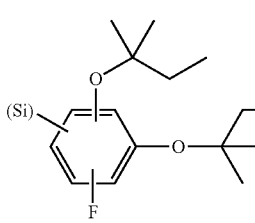
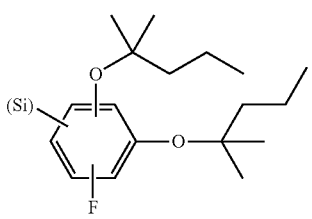

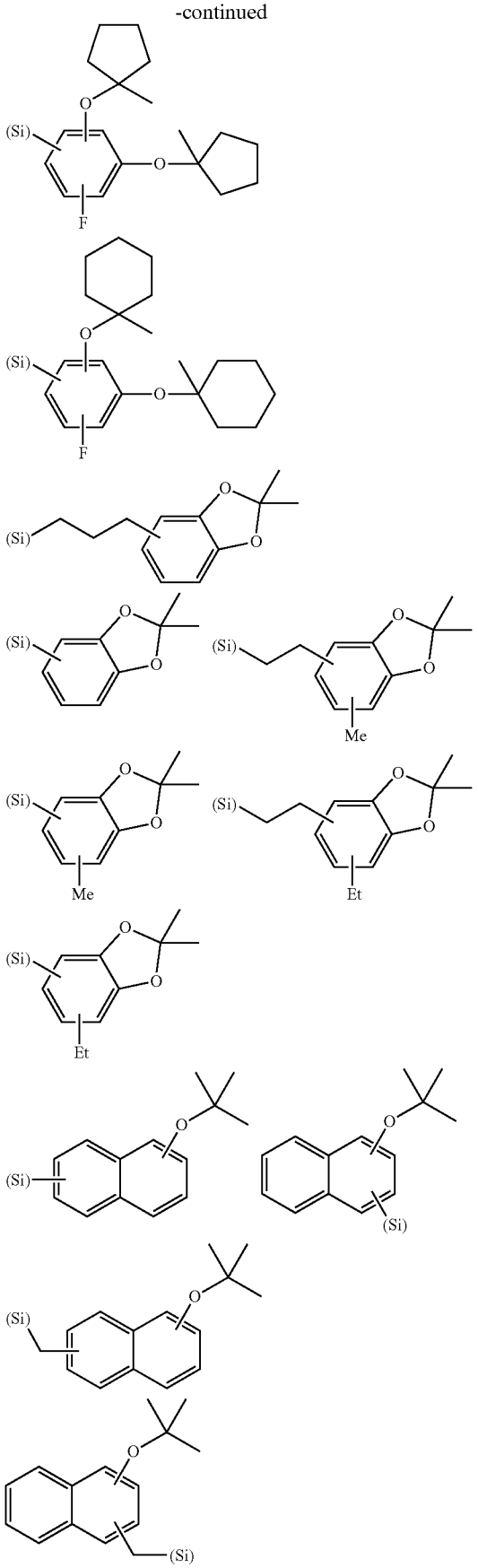
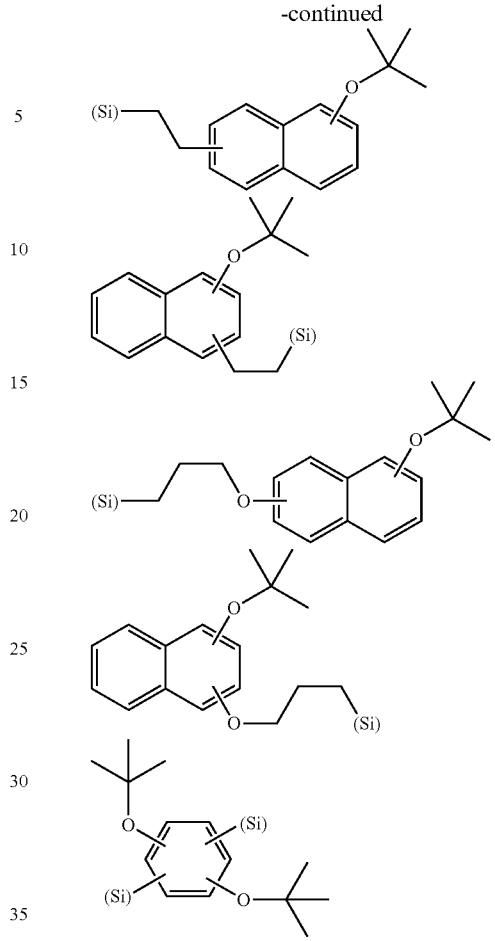

The polysiloxane contained in the composition for forming a resist under layer film of the present invention may contain a hydrolysable metal compound represented by the formula (B-2) as a starting material, in addition to the compound represented by the formula (B-1), $$L'(OR^{4B})_{B4}(OR^{5B})_{B5}(O)_{B6} \tag{B-2}$$

wherein $R^{4B}$ and $R^{5B}$ represent a hydrogen atom or an organic group having 1 to 30 carbon atoms; B4, B5, and B6 represent an integer of 0 or more, and B4+B5+B6 is a number of valency determined by L'; and L' represents an element belonging to the group III, IV, or V in the periodic table except for a carbon.

Examples of the hydrolysable metal compound represented by the formula (B-2) include the following compounds.

In the case that L' is boron, illustrative examples of the compound represented by the formula (B-2) include boron methoxide, boron ethoxide, boron propoxide, boron butoxide, boron amyloxide, boron hexyloxide, boron cyclopentoxide, boron cyclohexyloxide, boron allyloxide, boron phenoxide, boron methoxyethoxide, boric acid, and boron oxide.

In the case that L' is aluminum, illustrative examples of the compound represented by the formula (B-2) include aluminum methoxide, aluminum ethoxide, aluminum propoxide, aluminum butoxide, aluminum amyloxide, aluminum hexyloxide, aluminum cyclopentoxide, aluminum cyclohexyloxide, aluminum allyloxide, aluminum phenoxide, aluminum methoxyethoxide, aluminum ethoxyethoxide, aluminum dipropoxyethyl acetoacetate, aluminum dibutoxyethyl acetoacetate, aluminum propoxybisethyl acetoacetate, aluminum butoxybisethyl acetoacetate, aluminum 2,4-pentanedionate, and aluminum 2,2,6,6-tetramethyl-3,5-heptanedionate.

In the case that L' is gallium, illustrative examples of the compound represented by the formula (B-2) include gallium methoxide, gallium ethoxide, gallium propoxide, gallium butoxide, gallium amyloxide, gallium hexyloxide, gallium cyclopentoxide, gallium cyclohexyloxide, gallium allyloxide, gallium phenoxide, gallium methoxyethoxide, gallium ethoxyethoxide, gallium dipropoxyethyl acetoacetate, gallium dibutoxyethyl acetoacetate, gallium propoxybisethyl acetoacetate, gallium butoxybisethyl acetoacetate, gallium 2,4-pentanedionate, and gallium 2,2,6,6-tetramethyl-3,5-heptanedionate.

In the case that L' is yttrium, illustrative examples of the compound represented by the formula (B-2) include yttrium methoxide, yttrium ethoxide, yttrium propoxide, yttrium butoxide, yttrium amyloxide, yttrium hexyloxide, yttrium cyclopentoxide, yttrium cyclohexyloxide, yttrium allyloxide, yttrium phenoxide, yttrium methoxyethoxide, yttrium ethoxyethoxide, yttrium dipropoxyethyl acetoacetate, yttrium dibutoxyethyl acetoacetate, yttrium propoxybisethyl acetoacetate, yttrium butoxybisethyl acetoacetate, yttrium 2,4-pentanedionate, and yttrium 2,2,6,6-tetramethyl-3,5-heptanedionate.

In the case that L' is germanium, illustrative examples of the compound represented by the formula (B-2) include germanium methoxide, germanium ethoxide, germanium propoxide, germanium butoxide, germanium amyloxide, germanium hexyloxide, germanium cyclopentoxide, germanium cyclohexyloxide, germanium allyloxide, germanium phenoxide, germanium methoxyethoxide, and germanium ethoxyethoxide.

In the case that L' is titanium, illustrative examples of the compound represented by the formula (B-2) include titanium methoxide, titanium ethoxide, titanium propoxide, titanium butoxide, titanium amyloxide, titanium hexyloxide, titanium cyclopentoxide, titanium cyclohexyloxide, titanium allyloxide, titanium phenoxide, titanium methoxyethoxide, titanium ethoxyethoxide, titanium dipropoxybisethyl acetoacetate, titanium dibutoxybisethyl acetoacetate, titanium dipropoxybis-2,4-pentanedionate, and titanium dibutoxybis-2,4-pentanedionate.

In the case that L' is hafnium, illustrative examples of the compound represented by the formula (B-2) include hafnium methoxide, hafnium ethoxide, hafnium propoxide, hafnium butoxide, hafnium amyloxide, hafnium hexyloxide, hafnium cyclopentoxide, hafnium cyclohexyloxide, hafnium allyloxide, hafnium phenoxide, hafnium methoxyethoxide, hafnium ethoxyethoxide, hafnium dipropoxybisethyl acetoacetate, hafnium dibutoxybisethyl acetoacetate, hafnium dipropoxybis-2,4-pentanedionate, and hafnium dibutoxybis-2,4-pentanedionate.

In the case that L' is tin, illustrative examples of the compound represented by the formula (B-2) include tin methoxide, tin ethoxide, tin propoxide, tin butoxide, tin phenoxide, tin methoxyethoxide, tin ethoxyethoxide, tin 2,4-pentanedionate, and tin 2,2,6,6-tetramethyl-3,5-heptanedionate.

In the case that L' is arsenic, illustrative examples of the compound represented by the formula (B-2) include arsenic methoxide, arsenic ethoxide, arsenic propoxide, arsenic butoxide, and arsenic phenoxide.

In the case that L' is antimony, illustrative examples of the compound represented by the formula (B-2) include antimony methoxide, antimony ethoxide, antimony propoxide, antimony butoxide, antimony phenoxide, antimony acetate, and antimony propionate.

In the case that L' is niobium, illustrative examples of the compound represented by the formula (B-2) include niobium methoxide, niobium ethoxide, niobium propoxide, niobium butoxide, and niobium phenoxide.

In the case that L' is tantalum, illustrative examples of the compound represented by the formula (B-2) include tantalum methoxide, tantalum ethoxide, tantalum propoxide, tantalum butoxide, and tantalum phenoxide.

In the case that L' is bismuth, illustrative examples of the compound represented by the formula (B-2) include bismuth methoxide, bismuth ethoxide, bismuth propoxide, bismuth butoxide, and bismuth phenoxide.

In the case that L' is phosphorous, illustrative examples of the compound represented by the formula (B-2) include trimethylphosphite, triethylphosphite, tripropylphosphite, trimethylphosphate, triethyl-phosphate, tripropylphosphate, and diphosphorous-pentaoxide.

In the case that L' is vanadium, illustrative examples of the compound represented by the formula (B-2) include vanadium oxide bis(2,4-pentanedionate), vanadium 2,4-pentanedionate, vanadium tributoxide oxide, and vanadium tripropoxide oxide.

In the case that L' is zirconium, illustrative examples of the compound represented by the formula (B-2) include zirconium methoxide, zirconium ethoxide, zirconium propoxide, zirconium butoxide, zirconium phenoxide, zirconium dibutoxide bis(2,4-pentanedionate), and zirconium dipropoxide bis(2,2,6,6-tetramethyl-3,5-heptanedionate).

One or more compounds mentioned above may be selected and mixed before or during the reaction to be used as the starting material (monomer) for producing the polysiloxane.

The polysiloxane used in the composition for forming a resist under layer film of the present invention may be produced, for example, by hydrolysis condensation of the compounds represented by the formula (B-1), and if necessary, the compounds represented by the formula (B-2), by using one or more compounds selected from inorganic acid, aliphatic sulfonic acid, and aromatic sulfonic acid as an acid catalyst.

Illustrative examples of the acid catalyst used for the reaction include hydrofluoric acid, hydrochloric acid, hydrobromic acid, sulfuric acid, nitric acid, perchloric acid, phosphoric acid, methanesulfonic acid, benzenesulfonic acid, and toluenesulfonic acid. The amount of the catalyst to be used is usually in the range of $1\times10^{-6}$ to 10 mol, preferably $1\times10^{-5}$ to 5 mol, more preferably $1\times10^{-4}$ to 1 mol per 1 mol of the monomers.

The amount of water for obtaining the polysiloxane by hydrolysis condensation of these monomers is preferably in the range of 0.01 to 100 mol, more preferably 0.05 to 50 mol, much more preferably 0.1 to 30 mol per 1 mol of a hydrolysable substituent bonded to the monomers. If the amount is 100 mol or less, a reaction device does not become excessively large, therefore it is economical.

As an operation manner, the monomers are added to a catalyst aqueous solution to start hydrolysis condensation reaction. In the manner, an organic solvent may be added to the catalyst aqueous solution, the monomers may be diluted with an organic solvent, or both may be performed. The reaction temperature is preferably in the range of 0 to 100° C., and more preferably 5 to 80° C. A method including maintaining the temperature at 5 to 80° C. while the monomers are added dropwise, and then aging the mixture at 20 to 80° C. is preferable.

Illustrative examples of the organic solvent that can be added to the catalyst aqueous solution, or can dilute the monomers, include methanol, ethanol, 1-propanol, 2-propanol, 1-butanol, 2-butanol, 2-methyl-1-propanol, ethylene glycol, propylene glycol, acetone, acetonitrile, tetrahydrofuran, toluene, hexane, ethyl acetate, cyclohexanone, methylamyl ketone, butanediolmonomethyl ether, propyleneglycolmonomethyl ether, ethyleneglycolmonomethyl ether, butanediolmonoethyl ether, propyleneglycolmonoethyl ether, ethyleneglycolmonoethyl ether, butanediolmonopropyl ether, propyleneglycolmonopropyl ether, ethyleneglycolmonopropyl ether, propyleneglycoldimethyl ether, diethyleneglycoldimethyl ether, propyleneglycolmonomethyl ether acetate, propyleneglycolmonoethyl ether acetate, ethyl pyruvate, butyl acetate, methyl 3-methoxypropionate, ethyl 3-ethoxypropionate, t-butyl acetate, t-butyl propionate, propyleneglycolmono-t-butyl ether acetate, γ-butyrolactone, and mixture thereof.

Among them, water-soluble solvents are preferable. Illustrative examples thereof include alcohols such as methanol, ethanol, 1-propanol, and 2-propanol; polyvalent alcohols such as ethylene glycol and propylene glycol; polyvalent alcohol condensate derivatives such as butanediolmonomethyl ether, propyleneglycolmonomethyl ether, ethyleneglycolmonomethyl ether, butanediolmonoethyl ether, propyleneglycolmonoethyl ether, ethyleneglycolmonoethyl ether, butanediolmonopropyl ether, propyleneglycolmonopropyl ether, and ethyleneglycolmonopropyl ether; acetone; acetonitrile; tetrahydrofuran, etc. Particularly preferable is a solvent with a boiling point of 100° C. or less.

The amount of the organic solvent to be used is preferably in the range of 0 to 1,000 mL, and particularly preferably 0 to 500 mL per 1 mol of the monomers. If the amount is in such a range, a reaction vessel does not become excessively large, therefore it is economical.

Thereafter, if necessary, neutralization reaction of the catalyst is carried out, and alcohol produced by hydrolysis condensation reaction is removed under reduced pressure to obtain a reaction mixture aqueous solution. The amount of an alkaline substance to be used for neutralization is preferably 0.1 to 2 equivalent weight with respect to an acid used as the catalyst. The alkaline substance may be any substance so long as it shows basicity in water.

Subsequently, it is preferable that by-products such as alcohol produced by hydrolysis condensation reaction be removed from the reaction mixture. The temperature for heating the reaction mixture is preferably in the range of 0 to 100° C., more preferably 10 to 90° C., and much more preferably 15 to 80° C. though it is depending on the kinds of the added organic solvent and the alcohol produced by reaction. Degree of vacuum in this operation is preferably an atmospheric pressure or less, more preferably 80 kPa or less in the absolute pressure, and much more preferably 50 kPa or less in the absolute pressure though it is depending on the kinds of the organic solvent and the alcohol to be removed, an exhausting equipment, a condensation equipment, and heating temperature. Although it is difficult to know exactly the amount of the alcohol removed, it is preferable that about 80% by mass or more of the produced alcohol and so forth be removed.

Next, the acid catalyst used for hydrolysis condensation may be removed from the reaction mixture. A method for removing the acid catalyst may be to mix water and the polysiloxane, and then extract the polysiloxane by an organic solvent. As the organic solvent, an organic solvent that can dissolve the polysiloxane, and be separated into two layers when mixed with water is preferably used. Illustrative examples thereof include methanol, ethanol, 1-propanol, 2-propanol, 1-butanol, 2-butanol, 2-methyl-1-propanol, acetone, tetrahydrofuran, toluene, hexane, ethyl acetate, cyclohexanone, methylamyl ketone, butanediolmonomethyl ether, propyleneglycolmonomethyl ether, ethyleneglycolmonomethyl ether, butanediolmonoethyl ether, propyleneglycolmonoethyl ether, ethyleneglycolmonoethyl ether, butanediolmonopropyl ether, propyleneglycolmonopropyl ether, ethyleneglycolmonopropyl ether, propyleneglycoldimethyl ether, diethyleneglycoldimethyl ether, propyleneglycolmonomethyl ether acetate, propyleneglycolmonoethyl ether acetate, ethyl pyruvate, butyl acetate, methyl 3-methoxypropionate, ethyl 3-ethoxypropionate, t-butyl acetate, t-butyl propionate, propyleneglycolmono-t-butyl ether acetate, γ-butyrolactone, methylisobutyl ketone, cyclopentylmethyl ether, etc., and mixture thereof.

Moreover, a mixture of a water-soluble organic solvent and a slightly water-soluble organic solvent can also be used. Preferable examples thereof include methanol+ethyl acetate mixture, ethanol+ethyl acetate mixture, 1-propanol+ethyl acetate mixture, 2-propanol+ethyl acetate mixture, butanediolmonomethyl ether+ethyl acetate mixture, propyleneglycolmonomethyl ether+ethyl acetate mixture, ethyleneglycolmonomethyl ether+ethyl acetate mixture, butanediolmonoethyl ether+ethyl acetate mixture, propyleneglycolmonoethyl ether+ethyl acetate mixture, ethyleneglycolmonoethyl ether+ethyl acetate mixture, butanediolmonopropyl ether+ethyl acetate mixture, propyleneglycolmonopropyl ether+ethyl acetate mixture, ethyleneglycolmonopropyl ether+ethyl acetate mixture, methanol+methylisobutyl ketone mixture, ethanol+methylisobutyl ketone mixture, 1-propanol+methylisobutyl ketone mixture, 2-propanol+methylisobutyl ketone mixture, propyleneglycolmonomethyl ether+methylisobutyl ketone mixture, ethyleneglycolmonomethyl ether+methylisobutyl ketone mixture, propyleneglycolmonoethyl ether+methylisobutyl ketone mixture, ethyleneglycolmonoethyl ether+methylisobutyl ketone mixture, propyleneglycolmonopropyl ether+methylisobutyl ketone mixture, ethyleneglycolmonopropyl ether+methylisobutyl ketone mixture, methanol+cyclopentylmethyl ether mixture, ethanol+cyclopentylmethyl ether mixture, 1-propanol+cyclopentylmethyl ether mixture, 2-propanol+cyclopentylmethyl ether mixture, propyleneglycolmonomethyl ether+cyclopentylmethyl ether mixture, ethyleneglycolmonomethyl ether+cyclopentylmethyl ether mixture, propyleneglycolmonoethyl ether+cyclopentylmethyl ether mixture, ethyleneglycolmonoethyl ether+cyclopentylmethyl ether mixture, propyleneglycolmonopropyl ether+cyclopentylmethyl ether mixture, ethyleneglycolmonopropyl ether+cyclopentylmethyl ether mixture, methanol+propyleneglycolmethyl ether acetate mixture, ethanol+propyleneglycolmethyl ether acetate mixture, 1-propanol+propyleneglycolmethyl ether acetate mixture, 2-propanol+propyleneglycolmethyl ether acetate mixture, propyleneglycolmonomethyl ether+propyleneglycolmethyl ether acetate mixture, ethyleneglycolmonomethyl ether+propyleneglycolmethyl ether acetate mixture, propyleneglycolmonoethyl ether+propyleneglycolmethyl ether acetate mixture, ethyleneglycolmonoethyl ether+propyleneglycolmethyl ether acetate mixture, propyleneglycolmonopropyl ether+propyleneglycolmethyl ether acetate mixture, ethyleneglycolmonopropyl ether+propyleneglycolmethyl ether acetate mixture, etc., but are not restricted to the combination of these mixtures.

The mixing ratio of the water-soluble organic solvent and the slightly water-soluble organic solvent is appropriately determined. The amount of the water-soluble organic solvent is preferably in the range of 0.1 to 1,000 parts by mass, more preferably 1 to 500 parts by mass, and much more preferably 2 to 100 parts by mass, based on 100 parts by mass of the slightly water-soluble organic solvent.

Subsequently, the reaction mixture may be washed with neutral water. The neutral water may be water called deionized water or ultrapure water. The amount of the water is preferably in the range of 0.01 to 100 L, more preferably 0.05 to 50 L, and much more preferably 0.1 to 5 L per 1 L of the polysiloxane solution. The washing may be carried out in such a way that the both the polysiloxane solution and water are mixed in a vessel by stirring, and then settled to separate a water layer. The number of washing may be one or more, and preferably about 1 to 5 times because washing of 10 times or more is not worth to have full effects thereof.

Other methods for removing the acid catalyst include a method using an ion-exchange resin, and a method for removing an acid catalyst after neutralization with epoxy compounds such as ethylene oxide and propylene oxide. These methods can be appropriately selected according to the acid catalyst used in the reaction.

In the operation of water-washing, there is a case that a part of the polysiloxane escapes into a water layer, thereby substantially the same effect as fractionation operation is obtained. Therefore, the number of washing and the amount of water for washing may be appropriately determined in view of effects of catalyst removal and fractionation.

A final solvent is then added to the polysiloxane solution even when the acid catalyst remains therein or has been removed therefrom, and solvent-exchange is thereby performed under reduced pressure to obtain a desired solution of the polysiloxane. The temperature during the solvent-exchange is preferably in the range of 0 to 100° C., more preferably 10 to 90° C., and much more preferably 15 to 80° C. though it is depending on the kinds of the reaction solvent and the extraction solvent to be removed. Degree of vacuum in this operation is preferably an atmospheric pressure or less, more preferably 80 kPa or less in the absolute pressure, and much more preferably 50 kPa or less in the absolute pressure though it is depending on the kinds of the solvents to be removed, an exhausting equipment, condensation equipment, and heating temperature.

In this operation, sometimes the polysiloxane may become unstable because the solvent was exchanged. This occurs due to compatibility of the polysiloxane with the final solvent. Thus, in order to prevent this from occurring, a monovalent, divalent, or more polyvalent alcohol having cyclic ether as a substituent may be added thereto as a stabilizer. The amount thereof to be added is preferably in the range of 0 to 25 parts by mass, more preferably 0 to 15 parts by mass, and much more preferably 0 to 5 parts by mass, or 0.5 parts by mass or more when it is added, based on 100 parts by mass of the polysiloxane contained in the solution before the solvent-exchange. If necessary, a stabilizer may be added to the solution before the solvent-exchange operation.

The concentration of the polysiloxane solution is preferably in the range of 0.1 to 20% by mass. If the concentration is in such a range, condensation reaction of the polysiloxane does not progress; thereby the polysiloxane does not change to the state that it cannot be dissolved into an organic solvent again. Further, if the concentration is in such a range, the amount of the solvent becomes appropriate, therefore it is economical.

Preferable examples of the final solvent added to the polysiloxane solution include alcohol solvents, and particularly monoalkyl ether derivatives of ethylene glycol, diethylene glycol, triethylene glycol, propylene glycol, dipropylene glycol, butanediol, or the like. Illustrative examples thereof include butanediolmonomethyl ether, propyleneglycolmonomethyl ether, ethyleneglycolmonomethyl ether, butanediolmonoethyl ether, propyleneglycolmonoethyl ether, ethyleneglycolmonoethyl ether, butanediolmonopropyl ether, propyleneglycolmonopropyl ether, ethyleneglycolmonopropyl ether, etc.

In addition, if these solvents are a main solvent, a non-alcoholic solvent may be added thereinto as an adjuvant solvent. Illustrative examples of this adjuvant solvent include acetone, tetrahydrofuran, toluene, hexane, ethyl acetate, cyclohexanone, methylamyl ketone, propyleneglycoldimethyl ether, diethyleneglycoldimethyl ether, propyleneglycolmonomethyl ether acetate, propyleneglycolmonoethyl ether acetate, ethyl pyruvate, butyl acetate, methyl 3-methoxypropionate, ethyl 3-ethoxypropionate, t-butyl acetate, t-butyl propionate, propyleneglycolmono-t-butyl ether acetate, γ-butyrolactone, methylisobutyl ketone, cyclopentylmethyl ether, etc.

As an alternative operation manner, water or a water-containing organic solvent may be added to the monomers or an organic solution of the monomers to start hydrolysis reaction. In the manner, the catalyst may be added to the monomers or the organic solution of the monomers, or may be added to the water or the water-containing organic solvent. The reaction temperature is preferably in the range of 0 to 100° C., and more preferably 10 to 80° C. A method including heating the mixture at 10 to 50° C. while water is added dropwise, and then increasing the temperature to 20 to 80° C. to age the mixture is preferable.

As the organic solvent, water-soluble solvent is preferable, and illustrative examples thereof include alcohols such as methanol, ethanol, 1-propanol, 2-propanol, 1-butanol, 2-butanol, and 2-methyl-1-propanol; polyvalent alcohol condensate derivatives such as butanediolmonomethyl ether, propyleneglycolmonomethyl ether, ethyleneglycolmonomethyl ether, butanediolmonoethyl ether, propyleneglycolmonoethyl ether, ethyleneglycolmonoethyl ether, butanediolmonopropyl ether, propyleneglycolmonopropyl ether, ethyleneglycolmonopropyl ether, propyleneglycoldimethyl ether, diethyleneglycoldimethyl ether, propyleneglycolmonomethyl ether acetate, propyleneglycolmonoethyl ether acetate, and propyleneglycolmonopropyl ether; acetone; tetrahydrofuran; acetonitrile, etc., and a mixture thereof.

The amount of the organic solvent to be used may be the same amount as above. The obtained reaction mixture may be post-treated like the above-mentioned method to obtain the polysiloxane.

Alternatively, the polysiloxane used in the composition for forming a resist under layer film of the present invention may be produced, for example, by hydrolysis condensation of the compounds represented by the formula (B-1), and if necessary, the compounds represented by the formula (B-2), in the presence of a base catalyst.

Illustrative examples of the base catalyst include methylamine, ethylamine, propylamine, butylamine, ethylenediamine, hexamethylenediamine, dimethylamine, diethylamine, ethylmethylamine, trimethylamine, triethylamine, tripropylamine, tributylamine, cyclohexylamine, dicyclohexylamine, monoethanolamine, diethanolamine, dimethylmonoethanolamine, monomethyl-diethanolamine, triethanolamine, diazabicyclooctane, diazabicyclocyclononene, diazabicycloundecene, hexamethylenetetramine, aniline, N,N-dimethylaniline, pyridine, N,N-dimethylaminopyridine, pyrrole, piperazine, pyrrolidine, piperidine, picoline, tetramethylammonium hydroxide, choline hydroxide, tetrapropylammonium hydroxide, tetrabutylammonium hydroxide, ammonia, lithium hydroxide, sodium hydroxide, potassium hydroxide, barium hydroxide, calcium hydroxide, etc. The amount of the catalyst to be used is usually in the range of $1\times10^{-6}$ to 10 mol, preferably $1\times10^{-5}$ to 5 mol, more preferably $1\times10^{-4}$ to 1 mol per 1 mol of the monomers.

The amount of water for obtaining the polysiloxane by hydrolysis condensation of these monomers is preferably in the range of 0.1 to 50 mol per 1 mol of a hydrolysable substituent bonded to the monomers. If the amount is 50 mol or less, a reaction device does not become excessively large, therefore it is economical.

As an operation manner, the monomers are added to a catalyst aqueous solution to start hydrolysis condensation reaction. In the manner, an organic solvent may be added to the catalyst aqueous solution, the monomers may be diluted with an organic solvent, or both may be performed. The reaction temperature is preferably in the range of 0 to 100° C., and more preferably 5 to 80° C. A method including maintaining the temperature at 5 to 80° C. while the monomers are added dropwise, and then aging the mixture at 20 to 80° C. is preferable.

As the organic solvent that can be added to the base catalyst aqueous solution, or can dilute the monomers, the same solvents as those exemplified for the organic solvent that can be added to the acid catalyst aqueous solution are preferably used. The amount of the organic solvent to be used is preferably in the range of 0 to 1,000 mL, and particularly preferably 0 to 500 mL per 1 mol of the monomers. By using such an amount, a reaction vessel does not become excessively large, therefore it is economical.

Thereafter, if necessary, neutralization reaction of the catalyst is carried out, and alcohol produced by hydrolysis condensation reaction is removed under reduced pressure to obtain a reaction mixture aqueous solution. The amount of an acid substance to be used for neutralization is preferably 0.1 to 2 equivalent weight with respect to basic substance used as the catalyst. The acid substance may be any substance so long as it shows acidity in water.

Subsequently, it is preferable that by-products such as alcohol produced by hydrolysis condensation reaction be removed from the reaction mixture. The temperature for heating the reaction mixture and degree of vacuum may be the same temperature and degree of vacuum as in the case of using the acid catalyst.

Next, the base catalyst used for hydrolysis condensation may be removed from the reaction mixture. A method for removing the base catalyst may be to mix water and the polysiloxane, and then extract the polysiloxane by an organic solvent. As the organic solvent, the same solvent as those exemplified for the organic solvent used for removing the acid catalyst as mentioned above may be used.

Furthermore, a mixture of a water-soluble organic solvent and a slightly water-soluble organic solvent can also be used. As the mixture of a water-soluble organic solvent and a slightly water-soluble organic solvent, the same mixture as exemplified above for the mixture used for removing the acid catalyst may be used.

The mixing ratio of the water-soluble organic solvent and the slightly water-soluble organic solvent may be the same ratio as those used for removing the acid catalyst.

Subsequently, the reaction mixture may be washed with neutral water. The neutral water may be water called deionized water or ultrapure water. The amount of the water, the washing method, and the number of washing may be the same as in the case of using the acid catalyst.

Also, in the operation of water-washing, there is a case that a part of the polysiloxane escapes into a water layer, thereby substantially the same effect as fractionation operation is obtained. Therefore, the number of washing and the amount of water for washing may be appropriately determined in view of effects of catalyst removal and fractionation.

A final solvent is then added to the polysiloxane solution even when the base catalyst remains therein or has been removed therefrom, and solvent-exchange is thereby performed under reduced pressure to obtain a desired solution of the polysiloxane. The temperature and degree of vacuum during the solvent-exchange, and final concentration of the polysiloxane solution may be the same in the case of using the acid catalyst.

Also, the final solvent added to the polysiloxane solution may be the same as in the case of using the acid catalyst.

Moreover, a stabilizer may be added thereto like the case of using the acid catalyst.

As an alternative operation manner, water or a water-containing organic solvent may be added to the monomers or an organic solution of the monomers to start hydrolysis reaction. In the manner, the catalyst may be added to the monomers or the organic solution of the monomers, or may be added to the water or the water-containing organic solvent. The reaction temperature is preferably in the range of 0 to 100° C., and more preferably 10 to 80° C. A method including heating the mixture at 10 to 50° C. while water is added dropwise, and then increasing the temperature to 20 to 80° C. to age the mixture is preferable.

When the organic solvent is used, the same solvents as in the case of using the acid catalyst may be used.

The molecular weight of the polysiloxane thus obtained can be adjusted not only by selecting monomers, but also controlling reaction conditions during polymerization. The weight average molecular weight of the polysiloxane is preferably 100,000 or less, more preferably in the range of 200 to 50,000, and much more preferably 300 to 30,000. If the weight average molecular weight is 100,000 or less, generation of foreign matters and coating spots can be suppressed.

Meanwhile, the above weight average molecular weight is obtained as data, in terms of polystyrene as a reference material, by means of gel-permeation chromatography (GPC) using refractive index (RI) detector as a detector and tetrahydrofuran as an eluent.

[Other Additives]

To improve stability of the composition for forming a resist under layer film of the present invention, a monovalent, divalent or more polyvalent organic acid having 1 to 30 carbon atoms is preferably added thereto. Preferable examples of the organic acid include formic acid, acetic acid, propionic acid, butanoic acid, pentanoic acid, hexanoic acid, heptanoic acid, octanoic acid, nonanoic acid, decanoic acid, oleic acid, stearic acid, linoleic acid, linolenic acid, benzoic acid, phthalic acid, isophthalic acid, terephthalic acid, salicylic acid, trifluoroacetic acid, monochloroacetic acid, dichloroacetic acid, trichioroacetic acid, oxalic acid, malonic acid, methylmalonic acid, ethylmalonic acid, propylmalonic acid, butylmalonic acid, dimethylmalonic acid, diethylmalonic acid, succinic acid, methylsuccinic acid, glutaric acid, adipic acid, itaconic acid, maleic acid, fumaric acid, citraconic acid, citric acid, etc. Especially, oxalic acid, maleic acid, formic acid, acetic acid, propionic acid, citric acid, and the like are preferable. To keep stability, two or more kinds of these acids may be used as a mixture. The amount thereof to be added is preferably in the range of 0.001 to 25 parts by mass, more preferably 0.01 to 15 parts by mass, and much more preferably 0.1 to 5 parts by mass, based on 100 parts by mass of the polysiloxane contained in the composition.

Alternatively, the organic acid is preferably added such that pH of the composition becomes preferably $0 \leq pH \leq 7$, more preferably $0.3 \leq pH \leq 6.5$, and much more preferably $0.5 \leq pH \leq 6$.

Moreover, water may be added to the composition for forming a resist under layer film of the present invention. When water is added thereinto, the polysiloxane is hydrated whereby improving a lithography performance. Water content in the solvent component of the composition is preferably more than 0% and less than 50% by mass, more preferably in the range of 0.3 to 30% by mass, and much more preferably 0.5 to 20% by mass.

The amount of all solvents including water is preferably in the range of 100 to 100,000 parts by mass, and more preferably 200 to 50,000 parts by mass, based on 100 parts by mass of the base polymer (polysiloxane). By adding in such an amount, lithography performance can be improved, and uniformity of the coated film does not tend to be deteriorated, thereby causing of eye holes can be suppressed.

Also, a photo-acid generator may be added to the composition for forming a resist under layer film of the present invention. Illustrative examples of the photo-acid generator include those described in paragraphs (0160) to (0179) of Japanese Patent Laid-Open Publication No. 2009-126940.

Also, a stabilizer may be added to the composition for forming a resist under layer film of the present invention to improve stability of the composition. The stabilizer may be exemplified by ether compounds such as monovalent, divalent, or more polyvalent alcohols having cyclic ether as a substituent. Illustrative examples thereof include those described in paragraphs (0180) to (0184) of Japanese Patent Laid-Open Publication No. 2009-126940.

Also, a surfactant may be added to the composition for forming a resist under layer film of the present invention, if necessary. Illustrative examples of the surfactant include those described in paragraph (0185) of Japanese Patent Laid-Open Publication No. 2009-126940.

As described above, the composition for forming a resist under layer film of the present invention can form a resist under layer film that can suppress reflection particularly in lithography process by an ultraviolet laser such as ArF laser and KrF laser, and has excellent adhesiveness to a resist pattern formed thereon and excellent dry etching selectivity between the resist pattern formed thereon and an organic under layer film or the like formed thereunder.

<Patterning Process>

The present invention provides a patterning process comprising the steps of: forming an organic under layer film on a body to be processed by using a coating type organic under layer film material; forming a resist under layer film on the organic under layer film by using the above-described composition for forming a resist under layer film; forming a resist upper layer film on the resist under layer film; forming a resist pattern with the resist upper layer film; transferring the pattern to the resist under layer film by dry etching using the resist pattern as a mask; transferring the pattern to the organic under layer film by dry etching using the resist under layer film to which the pattern has been transferred as a mask; and further transferring the pattern to the body to be processed by dry etching using the organic under layer film to which the pattern has been transferred as a mask.

Here, as the body to be processed, a semiconductor apparatus substrate, a material in which any of a metal film, a metal carbide film, a metal oxide film, a metal nitride film, a metal oxycarbide film, and a metal oxynitride film is formed as a layer to be processed (a portion to be processed) on the semiconductor apparatus substrate, or the like may be used.

As the semiconductor substrate, a silicon substrate is generally used, but it is not particularly limited thereto, and a material such as Si, amorphous silicon ($\alpha$-Si), p-Si, $SiO_2$, SiN, SiON, W, TiN, Al, etc., and different in the material from the layer to be processed may be used.

Examples of a metal constituting the body to be processed include silicon, titanium, tungsten, hafnium, zirconium, chromium, germanium, copper, silver, gold, aluminum, indium, gallium, arsenic, palladium, iron, tantalum, iridium, molybdenum, and an alloy thereof. The layer to be processed may be made of Si, $SiO_2$, SiN, SiON, SiOC, p-Si, $\alpha$-Si, TiN, BPSG, SOG, Cr, CrO, CrON, MoSi, W, W—Si, Al, Cu, Al—Si, or the like; various low dielectric constant (low-k) films, or etching stopper film thereof. The thickness of the layer is preferably in the range of 50 to 10,000 nm, and more preferably 100 to 5,000 nm.

The resist under layer film used in the patterning process of the present invention can be formed on the organic under layer film that has been formed on the body to be processed, from the composition for forming a resist under layer film of the present invention, by using a spin-coating method or the like as well as a resist upper layer film (photoresist film). After spin coating, it is desired to be baked for evaporating the solvent, preventing from mixing with the resist upper layer film, and promoting cross-linking reaction. The baking temperature is preferably in the range of 50 to 500° C., and the heating time is preferably in the range of 10 to 300 seconds. Particularly preferable temperature range is 400° C. or less in order to reduce heat damage to the devices though it is depending on the structure of the devices to be fabricated.

Thus, when the resist under layer film is formed by using the composition for forming a resist under layer film of the present invention, a resist under layer film that can suppress reflection particularly in lithography process by an ultraviolet laser such as ArF laser and KrF laser, and has excellent adhesiveness to a resist pattern formed on the resist under layer film and excellent dry etching selectivity between the resist pattern (resist upper layer film) formed on the resist under layer film and the organic under layer film formed under the resist under layer film can be formed.

In the patterning process of the present invention, the resist pattern can be formed by a known method such as photolithography using a resist composition. For example, the resist pattern can be formed by forming a photoresist film on the resist under layer film from a chemically amplified resist composition, exposing the formed photoresist film to a high-energy beam after heat treatment, and then performing development. The development may be performed by positive development in which an exposed portion of the photoresist film is dissolved by using an alkaline developer, or may be performed by negative development in which an unexposed portion of the photoresist film is dissolved by using a developer consisting of an organic solvent.

In the patterning process of the present invention, the resist composition used in the above-mentioned lithography for forming the resist pattern is not particularly limited so long as it is a chemical amplified resist composition, and can form a pattern by positive development using an alkaline developer, or negative development using a developer consisting of an organic solvent.

As the lithography method using a high-energy beam, a lithography method using light having a wavelength of 300 nm or less is preferably used, and exposure process by KrF excimer laser beam is particularly preferable. In this case, a conventional resist composition for KrF excimer laser is preferably used for an upper layer photoresist film. Alternatively, ArF exposure can also be applied.

By using the patterning process of the present invention as mentioned above, a fine pattern can be formed on the substrate with high precision.

As mentioned above, when the ultraviolet absorber of the present invention is employed, for example, by adding it to a composition for forming a resist under layer film containing a polysiloxane, a resist under layer film that can suppress reflection by absorbing ultraviolet rays particularly in lithography process by an ultraviolet laser such as ArF laser and KrF laser, and exhibits excellent adhesiveness to a resist pattern formed thereon and high dry etching selectivity to both of the resist pattern formed thereon and an organic under layer film or the like formed thereunder, can be formed. Accordingly, when the formed resist pattern is sequentially transferred to the resist under layer film and the organic under layer film by dry etching process, the pattern can be transferred with a good pattern profile. In this way, the pattern formed in the upper layer resist can be finally transferred to the substrate with high precision.

EXAMPLES

Hereinafter, the present invention will be specifically described with reference to Synthesis Examples, Examples and Comparative Examples, but the present invention is not limited thereto.

[Synthesis of Compound Used for Ultraviolet Absorber]

The compounds (compound used for the ultraviolet absorber) represented by the formula (A-1) were synthesized in a manner shown below (Synthesis Examples 1-1 to 1-4).

Synthesis Example 1-1

Synthesis of Compound (D1)

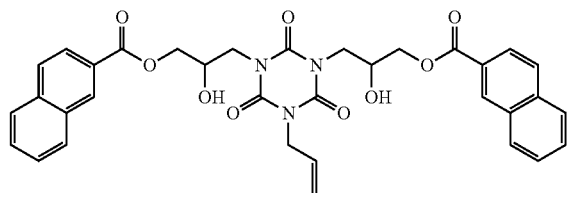

(1)

Under nitrogen atmosphere, into a three-necked flask equipped with a thermometer and a reflux condenser were placed 10.0 g (35.6 mmol) of MA-DGIC (available from Shikoku Chemicals Corporation), 12.2 g (71.1 mmol) of 2-naphthoic acid, and 50.0 g of PGME (1-methoxypropanol). After the temperature inside the flask was increased to 80° C. to homogenize the solution, 0.81 g (3.6 mmol) of benzyltriethylammonium chloride was added to perform the reaction at 130° C. for 6 hours in an oil bath. After completion of the reaction, the resultant was diluted with 200 mL of toluene, transferred to a separatory funnel, and washed with 50 mL of ultrapure water 4 times. The organic layer was collected, then concentrated and dried to obtain 20.9 g of Compound (D1).

The obtained compound was identified as Compound (D1) shown in the above structural formula by analysis using IR and $^1$H-NMR.

IR (ATR method): ν=3477, 3054, 2960, 1695, 1593, 1576, 1510, 1457, 1347, 1278, 1243, 1197, 1136, 1076, 1037, 1018, 934, 816, 784, 734 cm$^{-1}$ $^1$H-NMR (600 MHz in DMSO-d$_6$): δ=8.58 to 8.63 (2H, m), 8.0 to 8.15 (8H, m), 7.5 to 7.6 (4H, m), 5.6 to 5.8 (1H, m), 5.4 to 5.45 (2H, OH, m), 5.0 to 5.1 (2H, m), 4.0 to 4.3 (8H, m), 3.7 to 4.0 (4H, m) ppm Synthesis Example 1-2

Synthesis of Compound (D2)

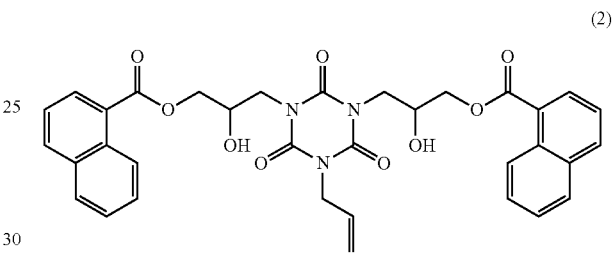

(2)

Synthesis was performed in the same manner as in Synthesis Example 1-1 except that 12.2 g of 1-naphthoic acid was used in place of 12.2 g of 2-naphthoic acid to obtain 21.0 g of Compound (D2).

The obtained compound was identified as Compound (D2) shown in the above structural formula by analysis using IR and $^1$H-NMR.

IR (ATR method): ν=3469, 3051, 2956, 1689, 1625, 1523, 1471, 1414, 1349, 1318, 1288, 1264, 1234, 1200, 1173, 1152, 1088, 1015, 893, 848, 793, 762, 733 cm$^{-1}$ $^1$H-NMR (600 MHz in DMSO-d$_6$): δ=8.6 to 8.8 (2H, m), 8.1 to 8.2 (4H, m), 7.5 to 7.7 (6H, m), 5.6 to 5.8 (1H, m), 5.35 to 5.5 (2H, OH, m), 5.05 to 5.20 (2H, m), 4.0 to 4.40 (8H, m), 3.7 to 3.95 (4H, m) ppm Synthesis Example 1-3

Synthesis of Compound (D3)

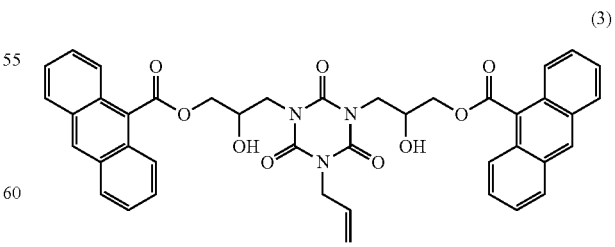

(3)

Synthesis was performed in the same manner as in Synthesis Example 1-1 except that 15.8 g of 9-anthracenecarboxylic acid was used in place of 12.2 g of 2-naphthoic acid to obtain 24.2 g of Compound (D3).

The obtained compound was identified as Compound (D3) shown in the above structural formula by analysis using IR, $^1$H-NMR, and $^{13}$C-NMR.

IR (ATR method): ν=3488, 3053, 2955, 1690, 1456, 1413, 1348, 1319, 1288, 1264, 1199, 1172, 1152, 1016, 893, 847, 793, 766, 733 cm$^{-1}$ $^1$H-NMR (600 MHz in DMSO-d$_6$): δ=8.75 (2H, s), 8.15 (4H, d), 8.09 (4H, d), 7.54 to 7.58 (8H, m), 5.70 (1H, m), 5.49 (2H, OH, d), 5.15 (1H, d), 5.07 (1H, d), 4.57 (4H, m), 4.15 to 4.25 (4H, m), 3.81 to 3.92 (4H, m) ppm $^{13}$C-NMR (150 MHz in DMSO-d$_6$): δ=168.51, 149.29, 148.76, 131.77, 130.39, 129.18, 128.85, 128.53, 127.65, 127.53, 127.24, 125.70, 124.83, 116.88, 67.31, 65.39, 44.5, 45.1 ppm Synthesis Example 1-4

Synthesis of Compound (D4)

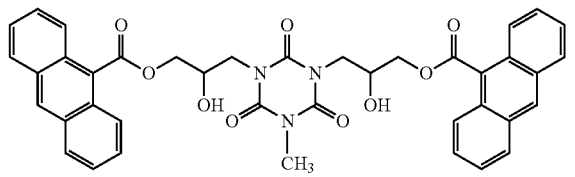

(4)

Synthesis was performed in the same manner as in Synthesis Example 1-1 except that 10.0 g of Me-DGIC (available from Shikoku Chemicals Corporation) was used in place of 10.0 g of MA-DGIC and 17.4 g of 9-anthracenecarboxylic acid was used in place of 12.2 g of 2-naphthoic acid to obtain 26.2 g of Compound (D4).

The obtained compound was identified as Compound (D4) shown in the above structural formula by analysis using IR, $^1$H-NMR, and $^{13}$C-NMR.

IR (ATR method): ν=3469, 3051, 2956, 1689, 1625, 1523, 1471, 1414, 1349, 1318, 1288, 1264, 1234, 1200, 1173, 1152, 1088, 1015, 893, 848, 793, 762, 733 cm$^{-1}$ $^1$H-NMR (600 MHz in DMSO-d$_6$): δ=8.76 (2H, s), 8.15 (4H, d), 8.08 (4H, d), 7.5 to 7.6 (8H, m), 5.47 (2H, OH, d-d), 4.5 to 4.6 (4H, m), 4.18 (2H, m), 3.75 to 3.9 (4H, m), 3.01 (3H, s-d) ppm $^{13}$C-NMR (150 MHz in DMSO-d$_6$): δ=168.49, 149.29, 149.19, 130.39, 129.21, 128.55, 127.63, 127.53, 127.25, 125.70, 124.82, 67.32, 65.37, 45.07, 45.06 ppm

[Synthesis of Polysiloxane]

The polysiloxanes represented by the formula (B-1) were synthesized in a manner shown below (Synthesis Examples 2-1 to 2-3).

Synthesis Example 2-1

Synthesis of Polysiloxane 1

To a mixture comprising 260 g of ethanol, 0.2 g of methanesulfonic acid, and 260 g of deionized water was added a mixture comprising 34.1 g of methyltrimethoxysilane and 52.2 g of tetraethoxysilane, and the resulting mixture was maintained at 40° C. for 12 hours to carry out hydrolysis condensation. After completion of the reaction, 300 g of propyleneglycolethyl ether (PGEE) was added thereto, and a by-produced alcohol and excess water were distilled off under reduced pressure to obtain 260 g of a PGEE solution containing Polysiloxane 1 (compound concentration: 11.2%). When the molecular weight of Polysiloxane 1 in terms of polystyrene was measured, it was Mw=2,300.

Synthesis Example 2-2

Synthesis of Polysiloxane 2

To a mixture comprising 260 g of ethanol, 0.2 g of methanesulfonic acid, and 260 g of deionized water was added a mixture comprising 5.0 g of phenyltrimethoxysilane and 99.2 g of tetraethoxysilane, and the resulting mixture was maintained at 40° C. for 12 hours to carry out hydrolysis condensation. After completion of the reaction, 300 g of propyleneglycolethyl ether (PGEE) was added thereto, and a by-produced alcohol and excess water were distilled off under reduced pressure to obtain 290 g of a PGEE solution containing Polysiloxane (compound concentration: 10.1%). When the molecular weight of Polysiloxane 2 in terms of polystyrene was measured, it was Mw=1,900.

Synthesis Example 2-3

Synthesis of Polysiloxane 3

To a mixture comprising 260 g of ethanol, 0.2 g of methanesulfonic acid, and 260 g of deionized water was added 68.1 g of methyltrimethoxysilane, and the resulting mixture was maintained at 40° C. for 12 hours to carry out hydrolysis condensation. After completion of the reaction, 300 g of propyleneglycolethyl ether (PGEE) was added thereto, and a by-produced alcohol and excess water were distilled off under reduced pressure to obtain 310 g of a PGEE solution containing Polysiloxane (compound concentration: 10.1%). When the molecular weight of Polysiloxane 3 in terms of polystyrene was measured, it was Mw=2,200.

Examples and Comparative Examples

Polysiloxanes 1 to 3 obtained in the above Synthesis Examples 2-1 to 2-3, Compounds (D1 to D4) obtained in the above Synthesis Examples 1-1 to 1-4 as an ultraviolet absorber, crosslinking accelerator, solvents, and additive (H$_2$O) were mixed with the ratios shown in Table 1, and the respective mixtures were filtered through 0.1 μm of a filter made of a fluorine resin to prepare the respective compositions for forming a resist under layer film, which were named Sols. 1 to 10.

TABLE 1

| No. | Polysiloxane (parts by mass) | Ultraviolet absorber (parts by mass) | Crosslinking accelerator (parts by mass) | Solvent (parts by mass) | Additive (parts by mass) |
|---|---|---|---|---|---|
| Sol. 1 | 1 (6.0) | D1 (0.6) | TPSMA (0.1) | PGEE (140) | H$_2$O (10) |
| Sol. 2 | 1 (6.0) | D2 (0.6) | TPSMA (0.1) | PGEE (140) | H$_2$O (10) |
| Sol. 3 | 1 (6.0) | D3 (0.6) | TPSOAc (0.1) | PGEE (140) | H$_2$O (10) |
| Sol. 4 | 1 (6.0) | D4 (0.6) | TPSOAc (0.1) | PGEE (140) | H$_2$O (10) |
| Sol. 5 | 2 (5.4) 3 (0.6) | D1 (0.6) | TPSMA (0.1) | PGEE (140) | H$_2$O (10) |

TABLE 1-continued

| No. | Polysiloxane (parts by mass) | Ultraviolet absorber (parts by mass) | Crosslinking accelerator (parts by mass) | Solvent (parts by mass) | Additive (parts by mass) |
|---|---|---|---|---|---|
| Sol. 6 | 2 (5.4) 3 (0.6) | D2 (0.6) | TPSMA (0.1) | PGEE (140) | H$_2$O (10) |
| Sol. 7 | 2 (5.4) 3 (0.6) | D3 (0.6) | TPSOAc (0.1) | PGEE (140) | H$_2$O (10) |
| Sol. 8 | 2 (5.4) 3 (0.6) | D4 (0.6) | TPSOAc (0.1) | PGEE (140) | H$_2$O (10) |
| Sol. 9 | 1 (6.0) | none | TPSMA (0.1) | PGEE (140) | H$_2$O (10) |
| Sol. 10 | 2 (5.4) 3 (0.6) | none | TPSMA (0.1) | PGEE (140) | H$_2$O (10) |

TPSMA: Mono(triphenylsulfonium) maleate
TPSOAc: Mono(triphenylsulfonium) acetate (Evaluation of Optical Characteristics)

Sols. 1 to 10 were each spin-coated, and heated at 200° C. for 60 seconds to form a polysiloxane-containing film with a film thickness of 80 nm (Films 1 to 10). Then, optical constants (refractive index: n and extinction coefficient: k) of Films 1 to 10 at a wavelength of 248 nm were measured by a variable angle spectroscopic ellipsometer (VUV-VASE manufactured by J.A. Woollam co., Inc.). The results are shown in Table 2.

TABLE 2

| Film | Refractive index: n | Extinction coefficient: k | Reflection |
|---|---|---|---|
| Example 1-1 | Film 1 | 1.61 | 0.05 | 1% or less |
| Example 1-2 | Film 2 | 1.60 | 0.06 | 1% or less |
| Example 1-3 | Film 3 | 1.46 | 0.08 | 1% or less |
| Example 1-4 | Film 4 | 1.46 | 0.11 | 1% or less |
| Example 1-5 | Film 5 | 1.46 | 0.07 | 1% or less |
| Example 1-6 | Film 6 | 1.46 | 0.06 | 1% or less |
| Example 1-7 | Film 7 | 1.47 | 0.06 | 1% or less |
| Example 1-8 | Film 8 | 1.47 | 0.05 | 1% or less |
| Comparative Example 1-1 | Film 9 | 1.52 | 0.00 | 1.5% or more |
| Comparative Example 1-2 | Film 10 | 1.52 | 0.00 | 1.5% or more |

As shown in Table 2, compared with Films 9 and 10 formed by using Sols. 9 and 10, which do not contain an ultraviolet absorber, Films 1 to 8 formed by using Sols. 1 to 8, which contain the ultraviolet absorber of the present invention, showed suppressed refractive index and good extinct coefficient, and reflection in KrF exposure was suppressed to 1% or less.

(Patterning Test)

A composition for forming a spin-on carbon film ODL-69 (Carbon content: 86% by mass) available from Shin-Etsu Chemical Co., Ltd., was applied onto a silicon wafer so as to have a film thickness of 2.0 μm, and heated at 300° C. for 60 seconds to form an organic under layer film. The compositions for forming a resist under layer film, Sols. 1 to 10, were each applied thereon, and heated at 200° C. for 60 seconds to form resist under layer films, Films 1 to 10, with a film thickness of 80 nm, respectively.

Subsequently, the KrF resist solution (PR-1) shown in Table 3 was applied onto Films 1 to 10, and baked at 100° C. for 90 seconds to form a photoresist film (resist upper layer film) having a film thickness of 250 nm.

Next, these were exposed by a KrF liquid immersion exposure apparatus (NSR-S206D manufactured by Nikon Corporation, NA=0.68), baked at 110° C. for 60 seconds (PEB), and developed by a 2.38% by mass tetramethylammonium hydroxide (TMAH) aqueous solution to obtain 130 nm line and space pattern. A cross-sectional shape of the wafer thus obtained was observed by an electron microscope (S-9380) manufactured by Hitachi Ltd. The results are shown in Table 4.

TABLE 3

| | Polymer (parts by mass) | Acid generator (parts by mass) | Base (parts by mass) | Surfactant (parts by mass) | Solvent A (parts by mass) | Solvent B (parts by mass) |
|---|---|---|---|---|---|---|
| PR-1 | KrF resist polymer (80) | PAG1(1) PAG2(2) | Base (0.2) | FC-4430 (0.5) | PGMEA (130) | Ethyl lactate (130) |

KrF resist polymer: Molecular weight (Mw)=15,000
Dispersity (Mw/Mn)=1.98

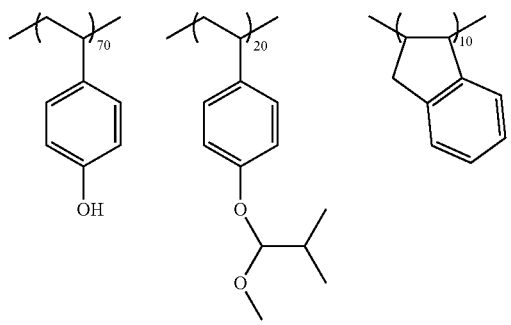

PAG1 (acid generator): (4-butoxyphenyl)diphenylsulfonium 10-camphorsulfonate

PAG2 (acid generator): bis(cyclohexylsulfonyl)-diazomethane

Base (basic compound): tris(2-methoxyethyl)amine

Surfactant: FC-4430 (available from Sumitomo 3M Inc.)

Solvent A: propyleneglycolmethyl ether acetate (PGMEA)

Solvent B: ethyl lactate

TABLE 4

| | Film | Pattern profile |
|---|---|---|
| Example 2-1 | Film 1 | Rectangular |
| Example 2-2 | Film 2 | Rectangular |
| Example 2-3 | Film 3 | Rectangular |
| Example 2-4 | Film 4 | Rectangular |
| Example 2-5 | Film 5 | Rectangular |
| Example 2-6 | Film 6 | Rectangular |
| Example 2-7 | Film 7 | Rectangular |

TABLE 4-continued

| | Film | Pattern profile |
|---|---|---|
| Example 2-8 | Film 8 | Rectangular |
| Comparative Example 2-1 | Film 9 | Tapered |
| Comparative Example 2-2 | Film 10 | Tapered |

As shown in Table 4, when a pattern was formed on the resist under layer film formed by using Sols. 9 and 10, which do not contain an ultraviolet absorber, the cross-sectional shape of the obtained pattern was tapered. In contrast, when a pattern was formed on the resist under layer film formed by using Sols. 1 to 8, which contain the ultraviolet absorber of the present invention, the cross-sectional shape of the obtained pattern was rectangular.

From the results mentioned above, it could be clarified that when a pattern is formed by using the composition for forming a resist under layer film containing the ultraviolet absorber of the present invention, reflection can be suppressed particularly in lithography process by an ultraviolet laser such as KrF laser, and a rectangular pattern can be formed. Further, it could be also clarified that the ultraviolet absorber of the present invention can be suitably used for photolithography using a resist under layer film containing a polysiloxane because even when added to a composition for forming a resist under layer film containing a polysiloxane, the ultraviolet absorber does not adversely affect dry etching mask properties and adhesiveness to a resist pattern formed on the resist under layer film.

It is to be noted that the present invention is not restricted to the foregoing embodiment. The embodiment is just an exemplification, and any examples that have substantially the same feature and demonstrate the same functions and effects as those in the technical concept described in claims of the present invention are included in the technical scope of the present invention.

What is claimed is:

1. An ultraviolet absorber comprising a compound represented by the formula (A-1), wherein three or more of $R^1$, $R^2$, $R^3$, and $R^4$ in the formula (A-1) are each selected from a naphthoyl group and an anthranoyl group,

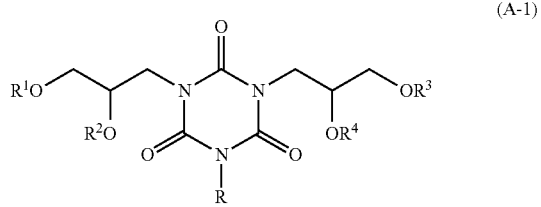

(A-1)

wherein R represents a methyl group, an ethyl group, a propyl group, or an allyl group; $R^1$, $R^2$, $R^3$, and $R^4$ may be the same or different, and each represent a hydrogen atom, a naphthoyl group, or an anthranoyl group; with the provisos that $R^1$ and $R^2$ are not a hydrogen atom at the same time; $R^3$ and $R^4$ are not a hydrogen atom at the same time.

2. A composition for forming a resist under layer film, comprising the ultraviolet absorber according to claim 1 and a polysiloxane.

3. The composition for forming a resist under layer film according to claim 2, wherein the polysiloxane contains one or more members selected from a condensate of the compound; and a hydrolysis condensate of the compound represented by the formula (B-1), $$R^{1B}{}_{B1}R^{2B}{}_{B2}R^{3B}{}_{B3}Si(OR^{OB})_{(4-B1-B2-B3)}$$ (B-1)

wherein $R^{OB}$ represents a hydrocarbon group having 1 to 6 carbon atoms; $R^{1B}$, $R^{2B}$, and $R^{3B}$ each represent a hydrogen atom or a monovalent organic group; and B1, B2, and B3 are each 0 or 1, and satisfy $0 \leq B1+B2+B3 \leq 3$.

4. A patterning process comprising the steps of:
forming an organic under layer film on a body to be processed by using a coating type organic under layer film material;
forming a resist under layer film on the organic under layer film by using the composition for forming a resist under layer film according to claim 3;
forming a resist upper layer film on the resist under layer film;
forming a resist pattern with the resist upper layer film;
transferring the pattern to the resist under layer film by dry etching using the resist pattern as a mask;
transferring the pattern to the organic under layer film by dry etching using the resist under layer film to which the pattern has been transferred as a mask; and further
transferring the pattern to the body to be processed by dry etching using the organic under layer film to which the pattern has been transferred as a mask.

5. The patterning process according to claim 4, wherein the body to be processed is a semiconductor apparatus substrate or a material in which any of a metal film, a metal carbide film, a metal oxide film, a metal nitride film, a metal oxycarbide film, and a metal oxynitride film is formed on the semiconductor apparatus substrate.

6. The patterning process according to claim 5, wherein a metal constituting the body to be processed comprises silicon, titanium, tungsten, hafnium, zirconium, chromium, germanium, copper, silver, gold, aluminum, indium, gallium, arsenic, palladium, iron, tantalum, iridium, molybdenum, or an alloy thereof.

7. A patterning process comprising the steps of:
forming an organic under layer film on a body to be processed by using a coating type organic under layer film material;
forming a resist under layer film on the organic under layer film by using the composition for forming a resist under layer film according to claim 2;
forming a resist upper layer film on the resist under layer film;
forming a resist pattern with the resist upper layer film;
transferring the pattern to the resist under layer film by dry etching using the resist pattern as a mask;
transferring the pattern to the organic under layer film by dry etching using the resist under layer film to which the pattern has been transferred as a mask; and further
transferring the pattern to the body to be processed by dry etching using the organic under layer film to which the pattern has been transferred as a mask.

8. The patterning process according to claim 7, wherein the body to be processed is a semiconductor apparatus substrate or a material in which any of a metal film, a metal carbide film, a metal oxide film, a metal nitride film, a metal oxycarbide film, and a metal oxynitride film is formed on the semiconductor apparatus substrate.

9. The patterning process according to claim 8, wherein a metal constituting the body to be processed comprises silicon, titanium, tungsten, hafnium, zirconium, chromium, germanium, copper, silver, gold, aluminum, indium, gallium, arsenic, palladium, iron, tantalum, iridium, molybdenum, or an alloy thereof.

10. A coating composition for forming a resist under layer film, comprising (1) an ultraviolet absorber containing a compound represented by the formula (A-1) and (2) a polysiloxane having a weight average molecular weight of 200-100,000,

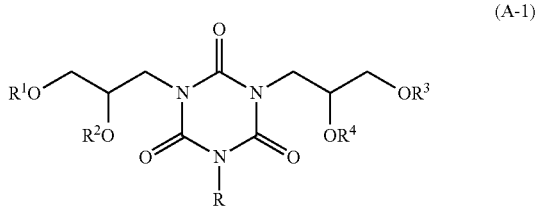

(A-1)

wherein R represents a methyl group, an ethyl group, a propyl group, or an allyl group; $R^1$, $R^2$, $R^3$, and $R^4$ may be the same or different, and each represent a hydrogen atom, a naphthoyl group, or an anthranoyl group; with the provisos that $R^1$ and $R^2$ are not a hydrogen atom at the same time; $R^3$ and $R^4$ are not a hydrogen atom at the same time.

11. The coating composition for forming a resist under layer film according to claim 10, wherein the polysiloxane contains one or more members selected from a condensate of the compound and a hydrolysis condensate of the compound represented by the formula (B-1), $$R^{1B}{}_{B1}R^{2B}{}_{B2}R^{3B}{}_{B3}Si(OR^{OB})_{(4-B1-B2-B3)}$$ (B-1)

wherein $R^{OB}$ represents a hydrocarbon group having 1 to 6 carbon atoms; $R^{1B}$, $R^{2B}$, and $R^{3B}$ each represent a hydrogen atom or a monovalent organic group; and B1, B2, and B3 are each 0 or 1, and satisfy $0 \leq B1+B2+B3 \leq 3$.

12. A patterning process comprising the steps of:
forming an organic under layer film on a body to be processed by using a coating type organic under layer film material;
forming a resist under layer film on the organic under layer film by using the composition for forming a resist under layer film according to claim 11;
forming a resist upper layer film on the resist under layer film;
forming a resist pattern with the resist upper layer film;
transferring the pattern to the resist under layer film by dry etching using the resist pattern as a mask;
transferring the pattern to the organic under layer film by dry etching using the resist under layer film to which the pattern has been transferred as a mask; and further
transferring the pattern to the body to be processed by dry etching using the organic under layer film to which the pattern has been transferred as a mask.

13. The patterning process according to claim 12, wherein the body to be processed is a semiconductor apparatus substrate or a material in which any of a metal film, a metal carbide film, a metal oxide film, a metal nitride film, a metal oxycarbide film, and a metal oxynitride film is formed on the semiconductor apparatus substrate.

14. The patterning process according to claim 13, wherein a metal constituting the body to be processed comprises silicon, titanium, tungsten, hafnium, zirconium, chromium, germanium, copper, silver, gold, aluminum, indium, gallium, arsenic, palladium, iron, tantalum, iridium, molybdenum, or an alloy thereof.

15. A patterning process comprising the steps of:
forming an organic under layer film on a body to be processed by using a coating type organic under layer film material;
forming a resist under layer film on the organic under layer film by using the composition for forming a resist under layer film according to claim 10;
forming a resist upper layer film on the resist under layer film;
forming a resist pattern with the resist upper layer film;
transferring the pattern to the resist under layer film by dry etching using the resist pattern as a mask;
transferring the pattern to the organic under layer film by dry etching using the resist under layer film to which the pattern has been transferred as a mask; and further
transferring the pattern to the body to be processed by dry etching using the organic under layer film to which the pattern has been transferred as a mask.

16. The patterning process according to claim 15, wherein the body to be processed is a semiconductor apparatus substrate or a material in which any of a metal film, a metal carbide film, a metal oxide film, a metal nitride film, a metal oxycarbide film, and a metal oxynitride film is formed on the semiconductor apparatus substrate.

17. The patterning process according to claim 16, wherein a metal constituting the body to be processed comprises silicon, titanium, tungsten, hafnium, zirconium, chromium, germanium, copper, silver, gold, aluminum, indium, gallium, arsenic, palladium, iron, tantalum, iridium, molybdenum, or an alloy thereof.

* * * * *